(12) United States Patent
Klinman et al.

(10) Patent No.: US 8,685,416 B2
(45) Date of Patent: Apr. 1, 2014

(54) COMPOSITIONS AND METHODS FOR THE TREATMENT OF CANCER

(75) Inventors: Dennis Klinman, Potomac, MD (US); Hidekazu Shirota, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/581,999

(22) PCT Filed: Mar. 1, 2011

(86) PCT No.: PCT/US2011/026727
§ 371 (c)(1),
(2), (4) Date: Aug. 30, 2012

(87) PCT Pub. No.: WO2011/109422
PCT Pub. Date: Sep. 9, 2011

(65) Prior Publication Data
US 2013/0012922 A1    Jan. 10, 2013

Related U.S. Application Data

(60) Provisional application No. 61/309,802, filed on Mar. 2, 2010.

(51) Int. Cl.
*A61K 39/00* (2006.01)
*A61K 48/00* (2006.01)

(52) U.S. Cl.
USPC ..................... 424/277.1; 514/44 R

(58) Field of Classification Search
None
See application file for complete search history.

(56) References Cited

U.S. PATENT DOCUMENTS

| 2003/0060440 A1 | 3/2003 | Klinman et al. |
| 2005/0026245 A1 | 2/2005 | Klinman et al. |
| 2006/0135459 A1 | 6/2006 | Epstein et al. |
| 2008/0031887 A1 | 2/2008 | Lustgarten |

FOREIGN PATENT DOCUMENTS

| WO | WO 98/18810 | 5/1998 |
| WO | WO 2004/084940 | 10/2004 |

OTHER PUBLICATIONS

Novakovic et al (Vaccine, 2007, 25(49): 8241-8256).*
Bae et al., "Photodynamic therapy-generated tumor cell lysates with CpG-Olgideoxynucleotide enhance immunotherapy efficacy in human papillomavirus 16 (E6/E7) immortalized tumor cells," *Cancer Sci.* 89:747-752 (2007).
Heit et al., "CpG-DNA Aided Cross-Priming by Cross-Presenting B Cells," *The Journal of Immunology* 172:1501-1507 (2004).
International Search Report from patent PCT Application No. PCT/US2011/026727, 4 pages (mailed on Sep. 19, 2011).
Jahrsdorfer et al., "B-Cell Lymphomas Differ in their Responsiveness to CpG Oligodeoxynucleotides," *Clinical Cancer Research* 11:1490-1499 (Feb. 15, 2005).
Nierkins et al., "In vivo Colocalization of Antigen and CpG within Dendritic Cells is Associated with the Efficacy of Cancer Immunotherapy," *Cancer Res.* 68:5390-96 (2008).
Novakovic et al., "Preventive and therapeutic antitumor effect of tumor vaccine composed of CpG ODN class C and irradiated tumor cells is triggered through the APCs and activation of CTLs," *Vaccine* 25: 8241-8256 (2007).
Ohashi et al., "Surgical excision combined with autologous whole tumor cell vaccination is an effective therapy for murine neuroblastoma," *Journal of Pediatric Surgery* 41:1361-1368 (2006).
Sandler et al., "CpG Oligonucleotides Enhance the Tumor Antigen-specific Immune Response of a Granulocyte Macrophage Colony-stimulating Factor-based Vaccine Strategy in Neuroblastoma," *Cancer Res.* 63:394-399 (2002).
Schirmbek et al., "Antigenic Epitopes Fused to Cationic Peptide Bound to Oligonucleotides Facilitate Toll-Like Receptor 9-Dependent, but $CD4^+$ T Cell Help-Independent, Priming of $CD8^+$ T Cells," *The Journal of Immunology* 171:5198-5207 (2003).
Shirota et al., "Suppressive Oligodexynucleotides Inhibit Th1 Differentiation by Blocking IFN-γ- and IL-12-Mediated Signaling," *Journal of Immunology* 173:5002-5007 (2004).
Shirota and Klinman, "CpG-conjugated apoptotic tumor cells elicit potent tumor-specific immunity," *Cancer Immunol Immunother* 60:659-669 (2011).
Wagner et al., "The Immunogenicity of CpG-antigen Conjugates," *Adv. Drug Deliv.* 61:243-247 (2009) (abstract only).
Wu et al., "In vivo Vaccination With Tumor Cell Lysate Plus CpG Oigodeoxynucletides Eradicates Murine Glioblastoma," *J. Immunother.* 30:789-797 (2007).
Zheng et al., "DNA containing CpG motifs induces angiogenesis," *PNAS* 99(13):8944-8949 (Jun. 25, 2002).

* cited by examiner

*Primary Examiner* — Sean Aeder
(74) *Attorney, Agent, or Firm* — Klarquist Sparkman, LLP

(57) ABSTRACT

Methods for inducing an immune response to a tumor in a subject are disclosed herein. These methods include selecting a subject with a tumor and administering a therapeutically effective amount of apoptotic tumor cells conjugated to a CpG oligodexoynucleotide (ODN) to the subject. In some embodiments, the CpG ODN is a K-type or a D-type CpG ODN. Methods for treating a tumor in a subject are also disclosed herein. These methods include selecting a subject with a tumor and administering a therapeutically effective amount of apoptotic tumor cells conjugated to a CpG oligodexoynucleotide (ODN) to the subject. In some embodiments, the tumor cells are autologous. In additional embodiments, the tumor is a lymphoma, cervical cancer, prostate cancer, breast cancer, colon cancer or a lung cancer.

34 Claims, 9 Drawing Sheets

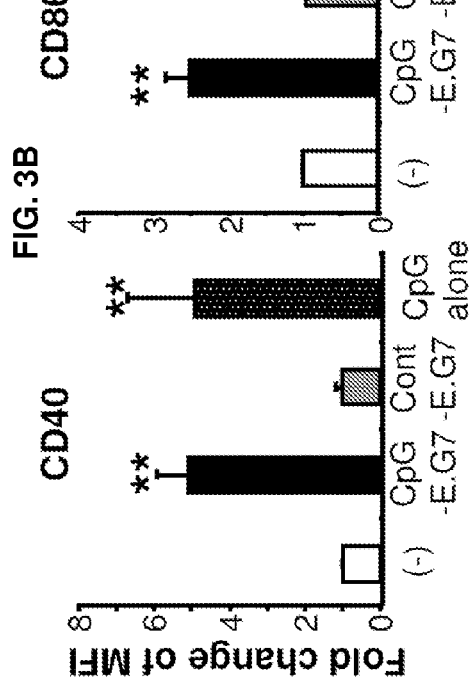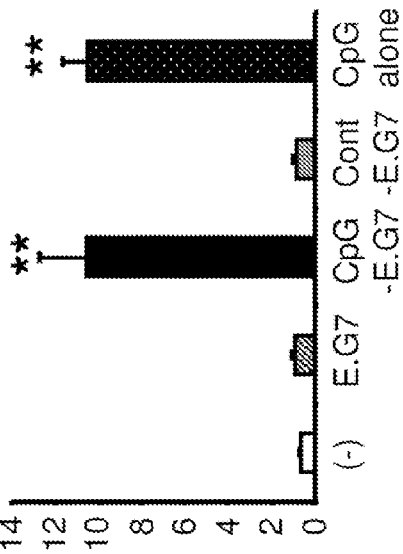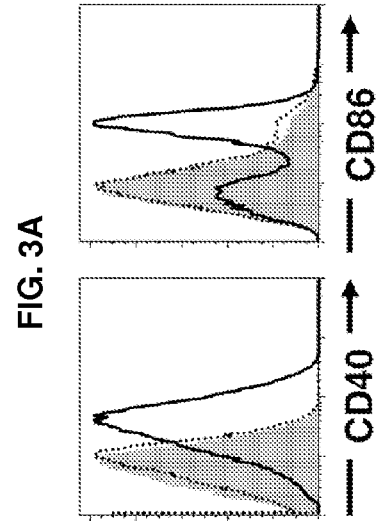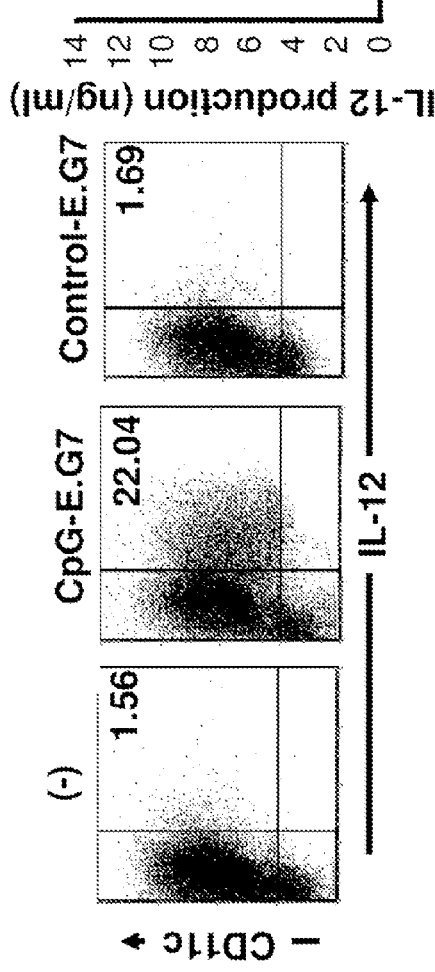
FIG. 3A
FIG. 3B
FIG. 3C
FIG. 3D

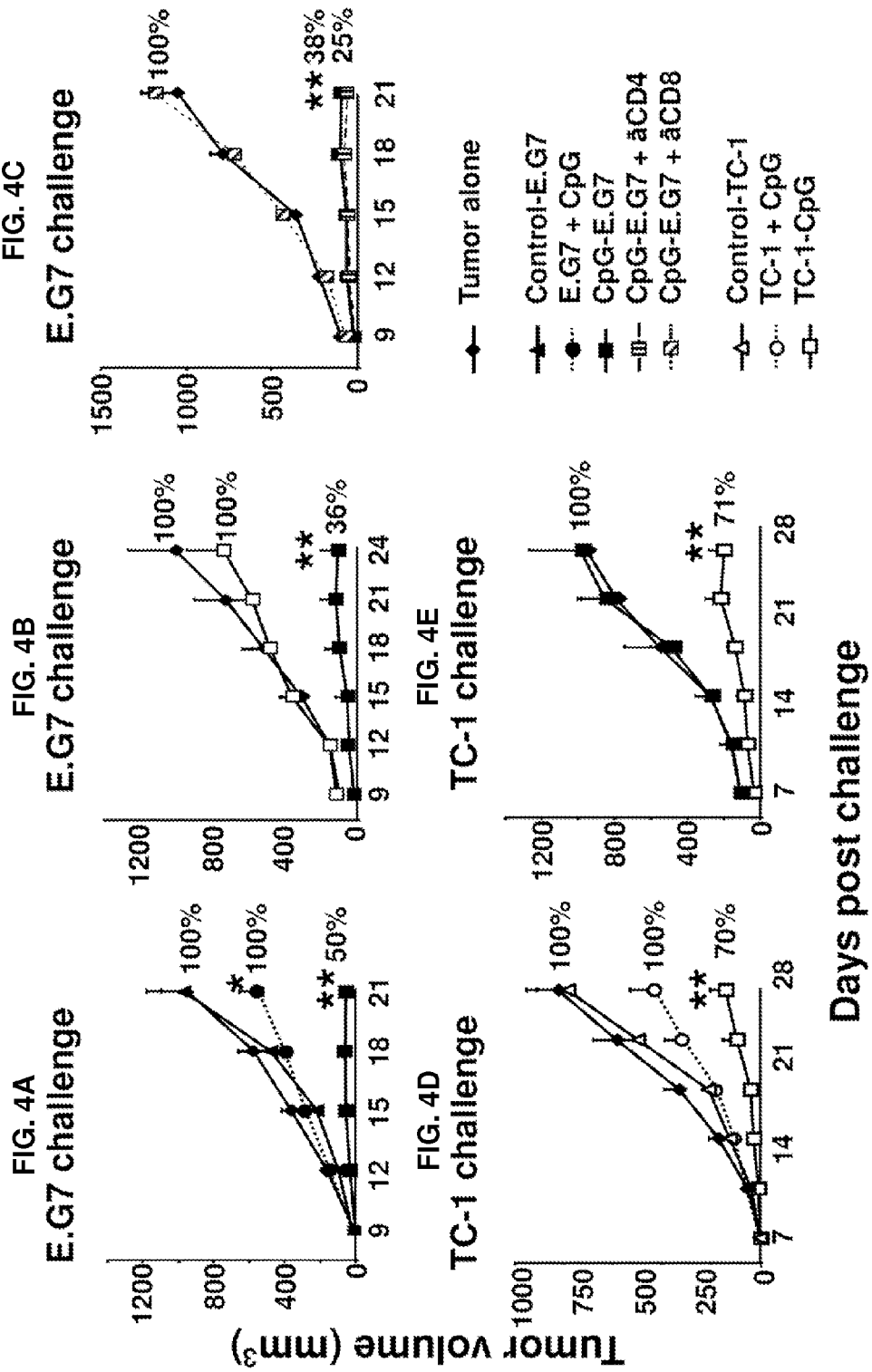

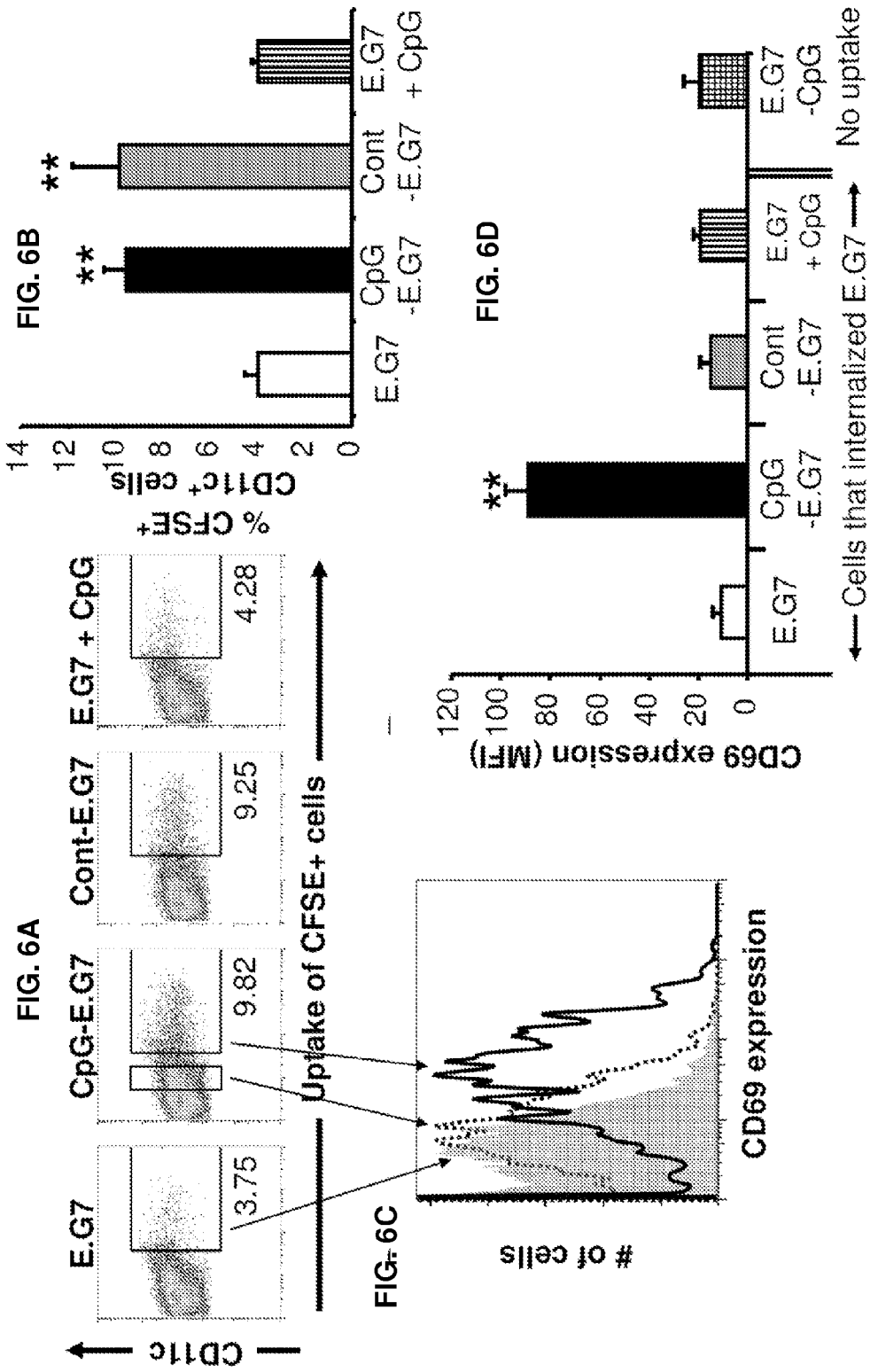

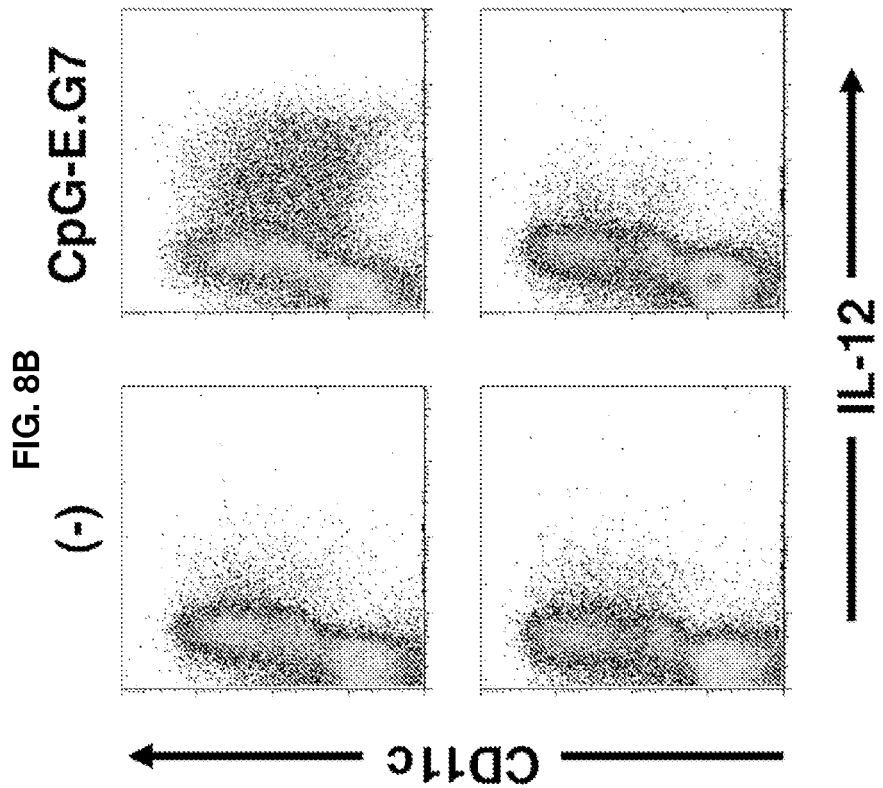
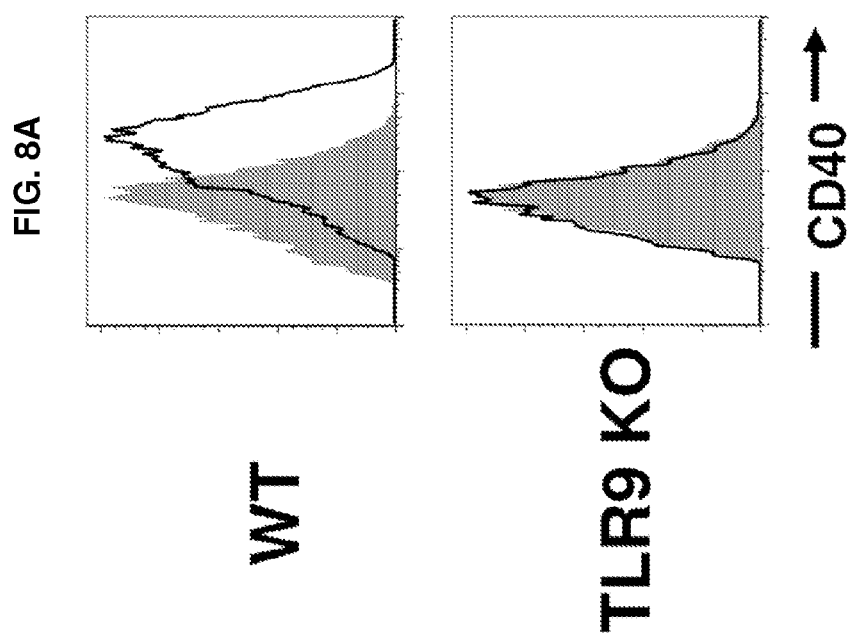

COMPOSITIONS AND METHODS FOR THE TREATMENT OF CANCER

CROSS REFERENCE TO RELATED APPLICATION

This is the U.S. national stage of PCT Application No. PCT/US2011/026727, filed on Mar. 1, 2011, which claims the benefit of U.S. Provisional Application No. 61/309,802, filed Mar. 2, 2010, which is incorporated by reference herein its entirety.

PRIORITY CLAIM

This claims the benefit of U.S. Provisional Application No. 61/309,802, filed Mar. 2, 2010, which is incorporated by reference herein it its entirety.

FIELD

This relates to the field of chemotherapy, specifically to methods for producing an immune response to tumor cells.

BACKGROUND

Cancer is the second leading cause of human death next to coronary disease in the United States. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. Cancer is soon predicted to become the leading cause of death.

Cancer is an abnormal state in which uncontrolled proliferation of one or more cell populations interferes with normal biological functioning. The proliferative changes are usually accompanied by other changes in cellular properties, including reversion to a less differentiated, more developmentally primitive state. The in vitro correlate of cancer is called cellular transformation. Transformed cells generally display several or all of the following properties: spherical morphology, expression of fetal antigens, growth-factor independence, lack of contact inhibition, anchorage-independence, and growth to high density.

Immunotherapy involves evoking an immune response against cancer cells based on their production of target antigens. Immunotherapy based on cell-mediated immune responses involves generating a cell-mediated response to cells that produce particular antigenic determinants, while immunotherapy based on humoral immune responses involves generating specific antibodies to cells that produce particular antigenic determinants.

Immunotherapies for preventing, ameliorating and/or treating cancer and tumors by means of using whole cell vaccines have the advantage of being multivalent with respect to tumor-antigens. However whole cell vaccines are usually only weakly immunogenic. Thus, a need remains for methods to increase the immunogenicity of this type of cancer vaccine.

SUMMARY

Methods for inducing an immune response to a tumor in a subject are disclosed herein. These methods include selecting a subject with a tumor and administering a therapeutically effective amount of non-viable tumor cells, such as apoptotic tumor cells, conjugated to one or more K-type CpG oligodexoynucleotides (ODNs), C-type or D-type CpG ODNs to the subject, thereby inducing an immune response to the tumor.

In some embodiments, the K-type CpG oligodeoxynucleotide has a nucleic acid sequence as set forth as 5' $N_1N_2N_3$D-CpG-W$N_4N_5N_6$ 3' (SEQ ID NO: 2), wherein the central CpG motif is unmethylated, D is T, G or A, W is A or T, and $N_1$, $N_2$, $N_3$, $N_4$, $N_5$, and $N_6$ are any nucleotides and wherein the CpG oligodeoxynucleotide is 10 to 30 nucleotides in length. In other embodiments, the D-type oligodeoxynucleotide includes an unmethylated CpG motif that has a sequence represented by the formula: 5' RY-CpG-RY3', wherein the central CpG motif is unmethylated, R is A or G (a purine), and Y is C or T (a pyrimidine). In other embodiments, the D-type oligodeoxynucleotide is at least about 16 nucleotides in length and includes a sequence represented by the Formula set forth as 5'-$X_1X_2X_3$ $Pu_1$ $Py_2$ CpG $Pu_3$ $Py_4$ $X_4X_5X_6(W)_M(G)_N$-3'(SEQ ID NO: 1), wherein the central CpG motif is unmethylated, Pu is a purine nucleotide, Py is a pyrimidine nucleotide, X and W are any nucleotide, M is any integer from 0 to 10, and N is any integer from 4 to 10. Combinations of K-type oligodeoxynucleotides and D-type oligodeoxynucleotides can also be used. C-type oligodeoxynucleotides can also be utilized in the methods disclosed herein.

Methods for treating a tumor in a subject are also disclosed herein. These methods include selecting a subject with a tumor and administering a therapeutically effective amount of non-viable tumor cells, such as apoptotic tumor cells conjugated to one or more K-type CpG oligodexoynucleotides, one or more D-type CpG oligodeoxynucletoides, or a combination of K-type and D-type oligodeoxynucleotides to the subject, thereby treating the tumor in the subject. In additional embodiments, the tumor cells are autologous. In additional embodiments, the tumor is a lymphoma, cervical cancer, prostate cancer, breast cancer, colon cancer or a lung cancer.

The foregoing and other objects, features, and advantages of the invention will become more apparent from the following detailed description, which proceeds with reference to the accompanying figures.

BRIEF DESCRIPTION OF THE DRAWINGS

FIGS. 3A-3D are graphs showing the activation of bone marrow derived DCs by CpG conjugated tumor cells. A) $5 \times 10^5$ apoptotic E.G7 cells were conjugated with 5 ug of control (dotted line) or CpG (solid line) ODN. The E.G7 cells were then cultured with $2 \times 10^6$ BMDCs for 16 hours. The expression of CD40 and CD86 by DCs (unstimulated cells shown in gray) was analyzed by flow cytometry. B) The experiment described in section (A) was repeated and the fold increase in CD40 and CD86 expression was calculated by comparison to unstimulated BMDCs in each experiment. Results represent the mean+SD increase in MFI from 6 independent studies. The effect of adding 5 ug of free CpG ODN during culture is also shown. C) $10^6$ BMDCs were cultured for 8 h with $2 \times 10^5$ E.G7 cells conjugated to control or CpG ODN (control-E.G7, CpG-E.G7). Brefeldin A was added during the final 4 hours of incubation. Cultures were stained to identify CD11c$^+$ DCs and for the presence of intracytoplasmic IL-12. Cell frequency is shown in the upper right corner of each dot plot. All experiments were repeated three times with similar results. D) $10^6$ BMDCs were cultured for 24 hours with 10 ug/ml of CpG ODN (CpG) or $2 \times 10^5$ E.G7 cells conjugated to the same amount of CpG or control ODN. The concentration of IL-12 in the supernatant of three independently studied samples per group (mean+SD) is shown. **; $p<0.01$ versus untreated group.

FIGS. 4A-4E are graphs showing results achieved using prophylactic treatment of tumors with ODN-conjugated vaccines. Congenic mice were immunized i.p. with $2 \times 10^6$ apoptotic tumor cells either mixed with free CpG ODN (tumor cell+CpG) or conjugated to CpG or control ODN (CpG-tumor cell; control-tumor cell). Vaccinations were on day −21 for the TC-1 vaccine and days −42 and −21 for the EG.7 vaccine. Three weeks after the final immunization mice were challenged with $3 \times 10^5$ tumor cells and monitored for tumor growth. Data represent the mean+SE of 7-14 mice per group from 2-3 independent experiments. The numbers to the right of each treatment are the percent of animals/group that developed tumors. Panel E shows the effect of depleting CD4$^+$ or CD8$^+$ T cells from immunized mice, as described in the methods section. *, $p<0.05$; **, $p<0.01$ (versus the untreated group)

FIGS. 6A-6D are graphs and a set of plots showing the effect of ODN conjugation on the uptake of apoptotic tumor cells by DCs in vivo. C57Bl/6 mice were immunized i.p. on days 0 and 21 with $10^7$ apoptotic E.G7 cells mixed with or conjugated to CpG or control ODN. Spleens were isolated 4 h (A and B) or 12 h (C and D) later, and DCs identified by staining with anti-CD11c and anti-CD69 mAbs. The uptake of CFSE-labeled E.G7 cells by CD11c$^+$ DCs (monitored by FACS) is shown in (A), and the mean+SD from four mice/group in (B). The expression of CD69 by DCs that had internalized CFSE-labeled tumor cells is shown by histogram in C while CD69 expression (MFI+SD) of 4 mice/group in (D). Note that CD11c$^+$ DCs in mice vaccinated with CpG-E.G7 that did not internalize tumor cells failed to up-regulate CD69.; $p<0.01$ (vs E.G7 group).

FIG. 8A-8B are a set of plots showing the effect of CpG-conjugated tumor cells on bone marrow derived dendritic cells (BMDCs) from TLR9 knock out (KO) mice. BMDCs from wild type (WT) and TLR9 KO mice were stimulated with CpG-E.G7 cells as described in FIG. 3. (A) The expression of CD40 (unstimulated cells shown in gray and CpG-E.G7 stimulated cells by solid line) was analyzed by flow cytometry. (B) Cultures were stained to identify CD11c$^+$ DCs and for the presence of intracytoplasmic IL-12.

SEQUENCE LISTING

Figure 1:
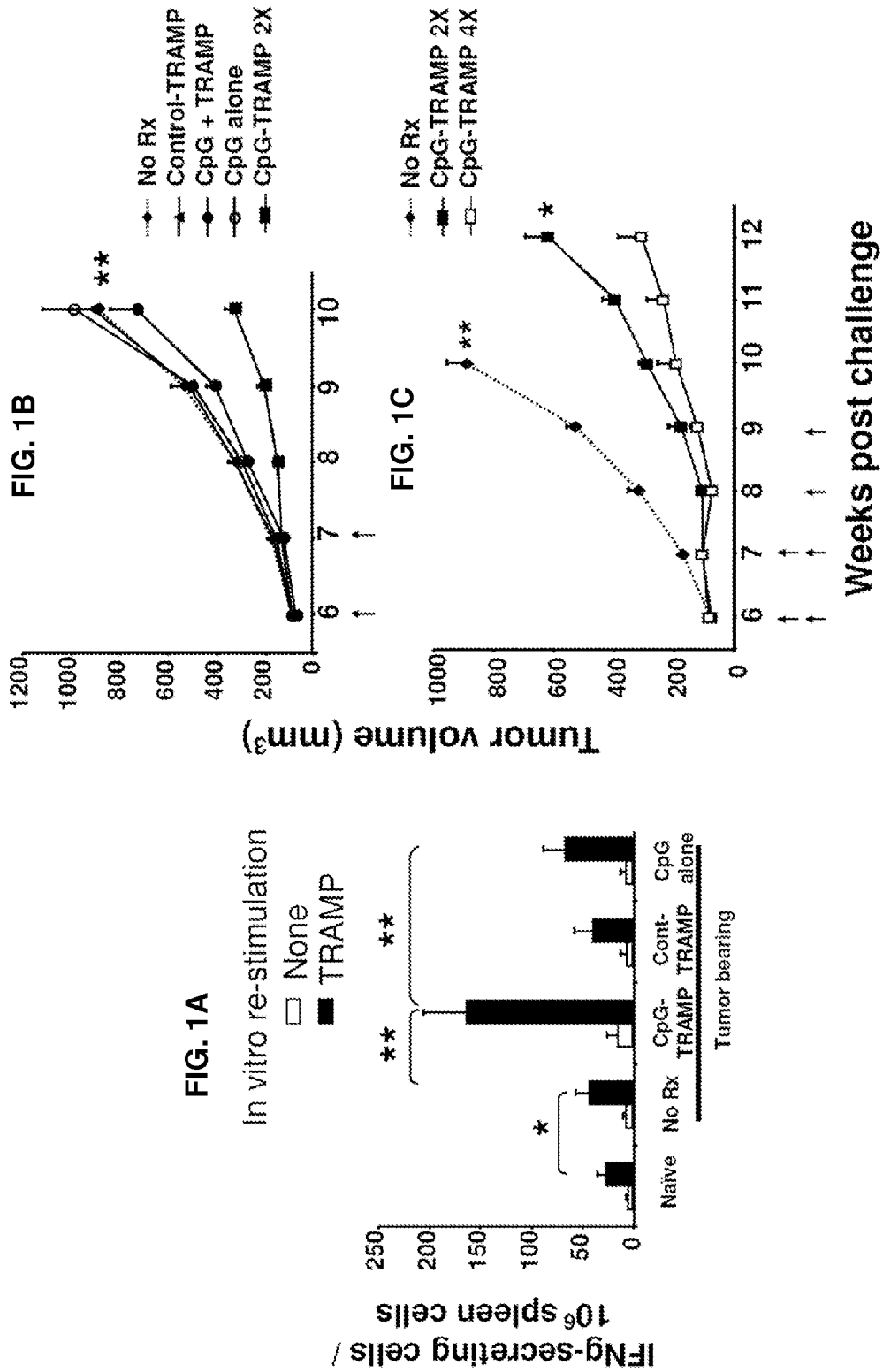
FIGS. 1A-1C are a set of graphs showing results achieved using treatment of established tumors with ODN-conjugated vaccine. $5 \times 10^5$ TRAMP C-1 cells were implanted into the flank of syngeneic mice on day 0. After the tumors became palpable (>5 mm in diameter at 5-6 wk) the mice were vaccinated intraperitoneally (i.p.) with $2 \times 10^6$ CpG or control ODN-conjugated TRAMP C-1 cells (CpG-TRAMP or cont-TRAMP), a mixture of free CpG ODN plus TRAMP C-1 cells (CpG+TRAMP) or 10 ug of CpG ODN alone. A) On day 60, spleen cells were isolated from unmanipulated mice (naive), mice implanted with TRAMP C-1 cells but not further treated (No Rx) or implanted with tumor cells and vaccinated twice. These cells were then stimulated in vitro with irradiated TRAMP C-1 cells and monitored for IFNg secretion by ELIspot assay. Results represent the mean+SD of 6-7 mice/group from three independent experiments. (B,C) Data show the mean+SE increase in tumor size of 6-14 mice per group derived by combining all results from 2 independent experiments (N=14; CpG-TRAMP 2×, N=14; No Rx group, N=10; CpG alone, N=9; control-TRAMP, N=7; CpG-TRAMP 4×, N=6; CpG+TRAMP). P values are in comparison to the group vaccinated 4 times. *, $p<0.05$; **, $p<0.01$

The Sequence Listing is submitted as an ASCII text file [4239-83797-03 Sequence Listing.txt, Aug. 27, 2012, 15.4 KB], which is incorporated by reference herein.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is a nucleic acid sequence of a D-type CpG oligodeoxynucleotide (ODN) sequence.

SEQ ID NOs: 2-33 are nucleic acid sequences of K-type CpG ODN.

SEQ ID NO: 34-35 are nucleic acid sequences of control ODN.

SEQ ID NO: 36 is an amino acid sequence of a synthetic peptide.

SEQ ID NO: 37 is the nucleic acid sequence of a K-type CpG ODN.

SEQ ID NOs: 38-62 are nucleic acid sequences of D-type CpG ODN

DETAILED DESCRIPTION

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments disclosed herein, the following explanations of specific terms are provided:

Antibody:

A protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is known to be a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

The term "antibody" includes both intact immunoglobulins as well as fragments produced by digestion with various peptidases. In one specific, non-limiting example, pepsin digests an antibody below the disulfide linkages in the hinge region to produce $F(ab)'_2$, a dimer of Fab' which itself is a light chain joined to $V_H$—$C_{H1}$ by a disulfide bond. The $F(ab)'_2$ may be reduced under mild conditions to break the disulfide linkage in the hinge region thereby converting the dimer into a Fab' monomer. The Fab' monomer is essentially a Fab with part of the hinge region (see Fundamental Immunology, W. E. Paul, ed., Raven Press, N.Y. (1993) for more antibody fragment terminology). While the Fab' fragment is defined in terms of the digestion of an intact antibody, one of skill will appreciate that such Fab' fragments may be synthesized de novo either chemically or by utilizing recombinant DNA methodology. An antibody that specifically binds a tumor binds selectively to that type of tumor and does not bind other cells, such as another type of tumor or normal cells of the same organ. For example, an antibody that specifically binds prostate cancer, lung cancer, lymphoma, breast cancer or colon cancer selectively binds prostate cancer, lung cancer, lymphoma, breast cancer or colon cancer, respectively, and does not bind normal prostate cells, lung cells, B or T cells, breast cells or colon cells.

Antigen:

A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. The term "antigen" includes all related antigenic epitopes. A "tumor antigen" is expressed on a specific type of tumor cells.

Animal:

Living multi-cellular vertebrate organisms, a category that includes, for example, mammals and birds. The term mammal includes both human and non-human mammals. Similarly, the term "subject" includes both human and veterinary subjects.

Apoptotic Cells:

Non-dividing, non-viable cells that can be distinguished from necrotic cells (other dead cells). Apoptosis is a result of programmed cell death. According to characteristic morphological and biochemical features, apoptosis is characterized by shrinkage of the cell, dramatic reorganization of the cell nucleus, cell membrane and cell metabolism, active membrane blebbing, and ultimate fragmentation of the cell into membrane-enclosed vesicles (apoptotic bodies). The nuclear events of apoptosis begin with collapse of the chromatin against the nuclear periphery and into one or a few large clumps within the nucleus. Nuclear features include chromatin aggregation followed by DNA fragmentation (a specific marker of apoptotic process) after activation of endonucleases resulting in multiples subunits of DNA of an approximately 180 basepairs. The cellular events include cytoplasmic condensation and partition of the cytoplasm and nucleus into membrane bound-vesicles which contain ribosomes, intact mitochondria and nuclear material which are surrounded by an intact cellular membrane (a specific marker of apoptotic process when compared with necrosis, the other non physiological cell death process).

Breast Cancer:

A neoplastic condition of breast tissue that can be benign or malignant. The most common type of breast cancer is ductal carcinoma. Ductal carcinoma in situ is a non-invasive neoplastic condition of the ducts. Lobular carcinoma is not an invasive disease but is an indicator that a carcinoma may develop. Infiltrating (malignant) carcinoma of the breast can be divided into stages (I, IIA, IIB, IIIA, IIIB, and IV).

Breast carcinomas lose the typical histology and architecture of normal breast glands. Generally, carcinoma cells overgrow the normal cells and lose their ability to differentiate into glandular like structures. The degree of loss of differentiation in general is related to the aggressiveness of the tumor. For example, "in situ" carcinoma by definition retains the basement membrane intact, whereas as it progresses to "invasive", the tumor shows breakout of basement membranes. Thus one would not expect to see, within breast carcinomas, staining of a discrete layer of basal cells as seen in normal breast tissue. For a discussion of the physiology and histology of normal breast and breast carcinoma, see Ronnov-Jessen, L., Petersen, O. W. & Bissell, M. J. Cellular changes involved in conversion of normal to malignant breast: importance of the stromal reaction (see, for example, Physiol Rev 76, 69-125, 1996).

Breast cancers can be divided into groups based on their expression profiles. Basal-type carcinomas usually are negative for expression of estrogen receptor (ER) and negative for expression of HER2 (erbB2) and progesterone receptor (PR), and thus are referred to as "triple-negative breast cancers" or "TNBC." This type of breast cancer is also denoted $ER^-$/$HER^-$/$PR^-$ and represents about 15-20% of all breast cancer, and generally cannot be treated using Her2 targeted or estrogen targeted therapies. It is believed that the aggressive nature of this cancer is correlated with an enrichment for cancer stem cells (CSC) with a $CD44^+CD24^{-/lo}$ phenotype. In some embodiments, basal carcinomas are negative for expression of progesterone receptor (PR), positive for expression of epidermal growth factor receptor (EGFR), and positive for expression of cytokeratin 5 (CK5). This phenotype is denoted as follows: ER−/PR−/HER−/CK5+/EGFR+.

"C" Class Oligodeoxynucleotides (ODNs):

ODNs that resemble K ODNs and are composed of only phosphorothiote nucleotides. Typically, C class ODNs have a TCGTCG motif at the 5' end and have a CpG motif imbedded in a palindromic sequence. Backbone modifications like 2'-O-methyl modifications especially in the 5' part of the ODN influence IFN-alpha-producing capacity of these ODN. C class ODNs have combined properties of D- and K-type ODNs. This class of ODNs stimulates B cells to secrete IL-6 and stimulates plasmacytoid dendritic cells to produce interferon-α. C class ODNs also induce IP-10 production and strong NK activation.

CpG or CpG Motif:

A nucleic acid having a cytosine followed by a guanine linked by a phosphate bond in which the pyrimidine ring of the cytosine is unmethylated. The term "methylated CpG" refers to the methylation of the cytosine on the pyrimidine ring, usually occurring at the 5-position of the pyrimidine ring. A CpG motif is a pattern of bases that include an unmethylated central CpG surrounded by at least one base flanking (on the 3' and the 5' side of) the central CpG. Without being bound by theory, the bases flanking the CpG confer a significant part of the activity to the CpG oligodeoxynucleotide. A CpG oligodeoxynucleotide is an oligodeoxynucleotide that is at least about ten nucleotides in length and includes an unmethylated CpG. CpG oligodeoxynucleotides include both D and K-type oligodeoxynucleotides (see below). CpG oligodeoxynucleotides are single-stranded. The entire CpG oligodeoxynucleotide can be unmethylated or portions may be unmethylated. In one embodiment, at least the C of the 5' CG 3' is unmethylated.

Cancer:

A malignant neoplasm that has undergone characteristic anaplasia with loss of differentiation, increase rate of growth, invasion of surrounding tissue, and is capable of metastasis. For example, thyroid cancer is a malignant neoplasm that arises in or from thyroid tissue, and breast cancer is a malignant neoplasm that arises in or from breast tissue (such as a ductal carcinoma). Residual cancer is cancer that remains in a subject after any form of treatment given to the subject to reduce or eradicate thyroid cancer. Metastatic cancer is a cancer at one or more sites in the body other than the site of origin of the original (primary) cancer from which the metastatic cancer is derived. Cancer includes, but is not limited to, solid tumors.

Chemotherapy; Chemotherapeutic Agents:

As used herein, any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating neoplasms such as solid tumors. In one embodiment, a chemotherapeutic agent is radioactive molecule. One of skill in the art can readily identify a chemotherapeutic agent of use (e.g. see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer L., Berkery R. (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). Chemotherapeutic agents include those known by those skilled in the art, including but not limited to: 5-fluorouracil (5-FU), azathioprine, cyclophosphamide, antimetabolites (such as Fludarabine), antineoplastics (such as Etoposide, Doxorubicin, methotrexate, and Vincristine), carboplatin, cis-platinum and the taxanes, such as taxol. Rapamycin has also been used as a chemotherapeutic.

Colon Cancer:

Colorectal cancer, also called large bowel cancer, includes cancerous growths in the colon, rectum and appendix. With 655,000 deaths worldwide per year, it is the third most common form of cancer and the second leading cause of cancer-related death in the Western world. Many colorectal cancers are thought to arise from adenomatous polyps in the colon. These mushroom-like growths are usually benign, but some may develop into cancer over time. The majority of the time, the diagnosis of localized colon cancer is through colonoscopy. Therapy is usually through surgery, which in many cases is followed by chemotherapy. The first symptoms of colon cancer are usually vague, such as bleeding, weight loss, and fatigue (tiredness). Local (bowel) symptoms are rare until the tumor has grown to a large size. Generally, the nearer the tumor is to the anus, the more bowel symptoms there will be.

Conjugated (Linked):

Two entities are conjugated when under physiological conditions of pH, ionic strength and osmotic potential, the majority of the entities are associated with each other at equilibrium, such as due to the presence of a convalent bond. Covalent linkage may be by any of a variety of chemical linking and cross-linking agents including, for example, homobifunctional or heterobifunctional crosslinking reagents, many of which are commercially available (see, e.g., Pierce Chemical Co. or Sigma Chemical Co.). Linking or crosslinking can be achieved by any of a variety of chemistries well known in the art including, for example, activated polyethylene glycols, aldehydes, isocyanates, maleimides and the like. Linking or cross-linking can also be achieved using physical methods, such as irradiation, for example gamma irradiation or ultraviolet (UV) irradiation.

Cytokine:

Proteins made by cells that affect the behavior of other cells, such as lymphocytes. In one embodiment, a cytokine is a chemokine, a molecule that affects cellular trafficking. Specific non-limiting examples of cytokines are IFNγ, IL-6, and IL-10.

D-Type Oligodeoxynucleotide (D ODN):

An oligodeoxynucleotide including an unmethylated CpG motif that has a sequence represented by the formula:

$$5'\ \text{RY-CpG-RY}\ 3'$$

wherein the central CpG motif is unmethylated, R is A or G (a purine), and Y is C or T (a pyrimidine). D-type oligodeoxynucleotides include an unmethylated CpG dinucleotide. Inversion, replacement or methylation of the CpG reduces or abrogates the activity of the D oligodeoxynucleotide.

In one embodiment, a D-type ODN is at least about 16 nucleotides in length and includes a sequence represented by Formula III:

(SEQ ID NO: 1)
$$5'-X_1X_2X_3\ Pu_1\ Py_2\ CpG\ Pu_3\ Py_4\ X_4X_5X_6(W)_M\ (G)_N-3'$$

wherein the central CpG motif is unmethylated, Pu is a purine nucleotide, Py is a pyrimidine nucleotide, X and W are any nucleotide, M is any integer from 0 to 10, and N is any integer from 4 to 10. Additional detailed description of D ODN sequences and their activities can be found in Verthelyi et al., *J. Immunol.* 166:2372-2377, 2001, which is herein incorporated by reference. Generally D ODNs can stimulate a cellular response. For example, D ODNs stimulate natural killer cells and the maturation of dendritic cells.

Epitope:

An antigenic determinant. These are particular chemical groups or peptide sequences on a molecule that are antigenic, i.e. that elicit a specific immune response. An antibody binds a particular antigenic epitope.

Functionally Equivalent:

Sequence alterations, for example in a K-type ODN that yield the same results as described herein. Such sequence alterations can include, but are not limited to, deletions, base modifications, mutations, labeling, and insertions.

Immune Response:

A response of a cell of the immune system, such as a B cell or T cell to a stimulus. In one embodiment, the response is specific for a particular antigen (an "antigen-specific response"). A "parameter of an immune response" is any particular measurable aspect of an immune response, including, but not limited to, cytokine secretion (IL-6, IL-10, IFNγ, etc.), immunoglobulin production, dendritic cell maturation, and proliferation of a cell of the immune system. One of skill in the art can readily determine an increase in any one of these parameters, using known laboratory assays. In one specific non-limiting example, to assess cell proliferation, incorporation of $^3$H-thymidine can be assessed. A "substantial" increase in a parameter of the immune response is a significant increase in this parameter as compared to a control. Specific, non-limiting examples of a substantial increase are at least about a 50% increase, at least about a 75% increase, at least about a 90% increase, at least about a 100% increase, at least about a 200% increase, at least about a 300% increase, and at least about a 500% increase. One of skill in the art can readily identify a significant increase using known statistical methods. One, specific, non-limiting example of a statistical test used to assess a substantial increase is the use of a Z test to compare the percent of samples that respond to an apoptotic cells conjugated to a K-type CpG ODN as compared to the percent of samples that respond using the another type of ODN, such as a D-type CpG ODN, or as compared to the K-type ODN alone (unconjugated). A non-parametric ANOVA can be used to compare differences in the magnitude of the response induced a apoptotic cell conjugated to a K-type CpG ODN as compared to the percent of samples that respond using the K-type CpG ODN alone. In this example, p≤0.05 is significant, and indicates a substantial increase in the parameter of the immune response. One of skill in the art can readily identify other statistical assays of use.

Isolated:

An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

K-Type Oligodeoxynucleotide (K ODN):

An oligodeoxynucleotide including an unmethylated CpG motif that has a sequence represented by the formula:

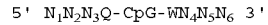

$$5' \; N_1N_2N_3Q\text{-}CpG\text{-}WN_4N_5N_6 \; 3'$$

wherein the central CpG motif is unmethylated, Q is T, G or A, W is A or T, and $N_1$, $N_2$, $N_3$, $N_4$, $N_5$, and $N_6$ are any nucleotides. In one embodiment, Q is a T. Additional description of K-type ODN sequences and their activities can be found in the description below. Generally K-type CpG ODNs can stimulate a humoral response. For example, K-type CpG ODNs stimulate the production of immunoglobulins, such as IgM and IgG. K-type CpG ODNs can also stimulate proliferation of peripheral blood mononuclear cells and increase expression of IL-6 and/or IL-12, amongst other activities.

Leukocyte:

Cells in the blood, also termed "white cells," that are involved in defending the body against infective organisms and foreign substances. Leukocytes are produced in the bone marrow. There are five main types of white blood cell, subdivided between 2 main groups: polymorphonuclear leukocytes (neutrophils, eosinophils, basophils) and mononuclear leukocytes (monocytes and lymphocytes). When an infection is present, the production of leukocytes increases.

Lung Cancer:

The main type of lung cancer is carcinoma of the lung, which includes small cell lung carcinoma and non-small cell lung carcinoma. Non-small cell lung carcinoma (NSCLC) is sometimes treated with surgery, while small cell lung carcinoma (SCLC) usually responds to chemotherapy and radiation. The most common cause of lung cancer is long-term exposure to tobacco smoke.

The non-small cell lung carcinomas are grouped together because their prognosis and management are similar. There are three main sub-types: squamous cell lung carcinoma, adenocarcinoma, and large cell lung carcinoma. Squamous cell lung carcinoma usually starts near a central bronchus. Cavitation and necrosis within the center of the cancer is a common finding. Well-differentiated squamous cell lung cancers often grow more slowly than other cancer types. Adenocarcinoma accounts for 29.4% of lung cancers. It usually originates in peripheral lung tissue. Most cases of adenocarcinoma are associated with smoking; however, among people who have never smoked, adenocarcinoma is the most common form of lung cancer. A subtype of adenocarcinoma, the bronchioloalveolar carcinoma, is more common in females.

Small cell lung cancers (SCLC, also called "oat cell carcinoma") is less common. It tends to arise in the larger airways (primary and secondary bronchi) and grows rapidly, becoming quite large. The "oat" cell contains dense neurosecretory granules (vesicles containing neuroendocrine hormones), which give this an endocrine/paraneoplastic syndrome association. While initially more sensitive to chemotherapy, it ultimately carries a worse prognosis and is often metastatic at presentation. Small cell lung cancers are divided into limited stage and extensive stage disease. This type of lung cancer also is strongly associated with smoking.

Lymphoma:

A cancer that begins in the lymphocytes and presents as a solid tumor of lymphoid cells. Lymphomas are generally treatable with chemotherapy, and in some cases radiotherapy and/or bone marrow transplantation, and can be curable, depending on the histology, type, and stage of the disease. The WHO classification is a generally accepted system for the classification of lymphoma and is based upon the foundations laid within the "Revised European-American Lymphoma classification" (REAL). This system attempts to group lymphomas by cell type (i.e. the normal cell type that most resembles the tumor) and defining phenotypic, molecular or cytogenetic characteristics. There are three large groups: the B cell, T cell, and natural killer cell tumors. Hodgkin's lymphoma, although considered separately within the WHO classification, is now recognized as being a tumor of lymphocytes of the mature B cell lineage.

Lymphomas include mature B cell lymphomas such as chronic lymphocytic leukemia/Small lymphocytic lymphoma, B-cell prolymphocytic leukemia, lymphoplasmacytic lymphoma (such as Waldenström macroglobulinemia), splenic marginal zone lymphoma, plasma cell neoplasms: plasma cell myeloma, plasmacytoma, monoclonal immunoglobulin deposition diseases, heavy chain diseases extranodal marginal zone B cell lymphoma, nodal marginal zone B cell lymphoma (NMZL), follicular lymphoma, mantle cell lymphoma, diffuse large B cell lymphoma, mediastinal (thymic) large B cell lymphoma, intravascular large B cell lymphoma, primary effusion lymphoma, and Burkitt lymphoma/leukemia. Lymphomas also include mature T cell and natural killer cell neoplasms, such as T cell prolymphocytic leukemia, T cell large granular lymphocytic leukemia, aggressive NK cell leukemia, adult T cell leukemia/lymphoma, extranodal NK/T cell lymphoma (nasal type), enteropathy-type T cell lymphoma, hepatosplenic T cell lymphoma, blastic NK cell lymphoma, mycosis fungoides/Sezary syndrome, primary cutaneous CD30-positive T cell lymphoproliferative disorders, primary cutaneous anaplastic large cell lymphoma, lymphomatoid papulosis, angioimmunoblastic T cell lymphoma, peripheral T cell lymphoma, and anaplastic large cell lymphoma.

Mammal:

This term includes both human and non-human mammals. Similarly, the term "subject" includes both human and veterinary subjects.

Necrotic Cells:

Necrosis of a cell typically begins with cell swelling, chromatin digestion, disruption of the plasma membrane and organelle membranes. Late necrosis is characterized by extensive DNA hydrolysis, vacuolation of the endoplasmic reticulum, organelle breakdown, and cell lysis. The intracellular contents are released from necrotic cells. The release of intracellular content after plasma membrane rupture can cause inflammation. Necrosis is cell death that is related to acute cell injury, and is caused by external factors, such as traumatic, injury infarction, infection, cancer, inflammation, toxins or trauma.

Neoplasm:

An abnormal cellular proliferation, which includes benign and malignant tumors, as well as other proliferative disorders.

Non-Viable Cells:

Cells that are in the process of dying or are dead. These cells do not divide. Non-viable cells include necrotic and apoptotic cells.

Nucleic Acid:

A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide or "Oligo":

Multiple nucleotides (i.e. molecules comprising a sugar (e.g. ribose or deoxyribose) linked to a phosphate group and to an exchangeable organic base, which is either a substituted pyrimidine (Py) (e.g. cytosine (C), thymine (T) or uracil (U)) or a substituted purine (Pu) (e.g. adenine (A) or guanine (G)). The term "oligonucleotide" as used herein refers to both oligoribonucleotides (ORNs) and oligodeoxynucleotides (ODNs). The term "oligonucleotide" also includes oligonucleosides (i.e. an oligonucleotide minus the phosphate) and any other organic base polymer. Oligonucleotides can be obtained from existing nucleic acid sources (e.g. genomic or cDNA), but are preferably synthetic (e.g. produced by oligonucleotide synthesis).

A "stabilized oligonucleotide" is an oligonucleotide that is relatively resistant to in vivo degradation (for example via an exo- or endo-nuclease). In one embodiment, a stabilized oligonucleotide has a modified phosphate backbone. One specific, non-limiting example of a stabilized oligonucleotide has a phosphorothioate modified phosphate backbone (wherein at least one of the phosphate oxygens is replaced by sulfur). Other stabilized oligonucleotides include: nonionic DNA analogs, such as alkyl- and aryl-phosphonates (in which the charged phosphonate oxygen is replaced by an alkyl or aryl group), phophodiester and alkylphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

An "immunostimulatory oligodeoxynucleotide," "immunostimulatory CpG containing oligodeoxynucleotide," "CpG ODN," refers to an oligodeoxynucleotide, which contains a cytosine, guanine dinucleotide sequence and (e.g. has a mitogenic effect or induces cytokine production) vertebrate immune cells. In one embodiment, an immunostimulatory CpG ODN stimulates a parameter of an immune response in a subject. The cytosine, guanine is unmethylated.

An "oligonucleotide delivery complex" is an oligonucleotide associated with (e.g. ionically or covalently bound to or encapsulated within) a targeting agent (e.g. a molecule that results in a higher affinity binding to a target cell (e.g. B-cell or natural killer (NK) cell) surface and/or increased cellular uptake by target cells). Examples of oligonucleotide delivery complexes include oligonucleotides associated with: a sterol (e.g. cholesterol), a lipid (e.g. cationic lipid, virosome or liposome), or a target cell specific binding agent (e.g. a ligand recognized by a target cell specific receptor). Preferred complexes must be sufficiently stable in vivo to prevent significant uncoupling prior to internalization by the target cell. However, the complex should be cleavable or otherwise accessible under appropriate conditions within the cell so that the oligonucleotide is functional. (Gursel, J. Immunol. 167:3324, 2001).

Pharmaceutical Agent or Drug:

A chemical compound or composition capable of inducing a desired therapeutic or prophylactic effect when properly administered to a subject. Pharmaceutical agents include, but are not limited to, chemotherapeutic agents and anti-infective agents.

Pharmaceutically Acceptable Carriers:

The pharmaceutically acceptable carriers useful in the methods and compositions disclosed herein are conventional. Remington's Pharmaceutical Sciences, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing or Treating a Disease:

"Preventing" a disease refers to inhibiting the full development of a disease, for example in a person who is known to have a predisposition to a disease such as a cancer. An example of a person with a known predisposition is someone with a history of breast cancer in the family, or who has been exposed to factors that predispose the subject to a condition, such as melanoma. "Treatment" refers to a therapeutic intervention that ameliorates a sign or symptom of a disease or pathological condition after it has begun to develop. In several embodiments, treatment refers to a reduction in size of a tumor, a decrease in the number and/or size of metastases, or a decrease in a symptom of the tumor.

Purified:

The term purified does not require absolute purity; rather, it is intended as a relative term. Thus, for example, a purified peptide preparation is one in which the peptide or protein is more enriched than the peptide or protein is in its natural environment within a cell. Preferably, in a purified preparation, the protein or peptide represents at least 50% of the total peptide or protein content of the preparation. Similarly, in a purified preparation of oligodeoxynucleotides, the oligodeoxynucleotide represents at least 50% of the total nucleic acid content of the preparation.

Self-Complementary Nucleic Acid Sequence:

A nucleic acid sequence that can form Watson-Crick base pairs. The four bases characteristic of deoxyribonucleic acid unit of DNA are the purines (adenine and guanine) and the pyrimidines (cytosine and thymine). Adenine pairs with thymine via two hydrogen bonds, while guanine pairs with cytosine via three hydrogen bonds. If a nucleic acid sequence includes two or more bases in sequence that can form hydrogen bonds with two or more other bases in the same nucleic acid sequence, then the nucleic acid includes a self-complementary sequence. In several embodiments, a self-complementary nucleic acid sequence includes 3, 4, 5, 6 or more bases that could form hydrogen bonds with 3, 4, 5, 6 or more bases, respectively, of the same nucleic acid sequence.

Specific Binding:

Binding which occurs between such paired species as enzyme/substrate, receptor/agonist, receptor/ligand, antibody/antigen, and lectin/carbohydrate which may be mediated by covalent or non-covalent interactions or a combination of covalent and non-covalent interactions. When the interaction of the two species produces a non-covalently bound complex, the binding that occurs is typically electrostatic, hydrogen-bonding, or the result of lipophilic interactions. Accordingly, "specific binding" occurs between a paired species where there is interaction between the two that produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

Therapeutically Effective Dose:

A dose sufficient to prevent advancement, or to cause regression of a disease, or which is capable of relieving symptoms caused by a disease, such as pain.

Tumor:

An abnormal growth of cells, which can be benign or malignant. Cancer is a malignant tumor, which is characterized by abnormal or uncontrolled cell growth. Other features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma). In several examples, a tumor is melanoma, lung cancer, lymphoma breast cancer or colon cancer.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

DETAILED DESCRIPTION

Methods for inducing an immune response to a tumor in a subject are disclosed herein. These methods include selecting a subject with a tumor and administering a therapeutically effective amount of apoptotic tumor cells conjugated to a CpG oligodexoynucleotide (ODN) to the subject, thereby inducing an immune response to the tumor. The CpG ODN can be any type of ODN, including K, D, and C-type CpG ODN.

In additional embodiments, the tumor cells are autologous. In additional embodiments, the tumor is a lymphoma, cervical cancer, prostate cancer, breast cancer, colon cancer or a lung cancer. The methods are of use to treat or prevent tumors in a subject, including benign and malignant tumors. The methods are also of use to decrease the size and/or number of metastases.

K-Type CpG ODN

In several embodiments, a K-type CpG ODN or a mixture of K-type CpG ODNs is utilized in the methods disclosed herein. Briefly, the K-type CpG ODN nucleic acid sequences useful in the methods disclosed herein are represented by the formula:

5'-$N_1DCGYN_2$-3' wherein at least one nucleotide separates consecutive CpGs; D is adenine, guanine, or thymidine; Y is cytosine or thymine, N is any nucleotide and $N_1+N_2$ is from about 0-26 bases. In one embodiment, $N_1$ and $N_2$ do not contain a CCGG quadmer or more than one CGG trimer; and the nucleic acid sequence is from about 8-30 bases in length, such as about 10 to 30 nucleotides in length. However, nucleic acids of any size (even many kb long) can be used in the methods disclosed herein if CpGs are present. In one embodiment, synthetic oligonucleotides of use do not include a CCGG quadmer or more than one CCG or CGG trimer at or near the 5' or 3' terminals and/or the consensus mitogenic CpG motif is not a palindrome. A "palindromic sequence" or "palindrome" means an inverted repeat (i.e., a sequence such as ABCDEE'D'C'B'A', in which A and A' are bases capable of forming the usual Watson-Crick base pairs).

In another embodiment, the methods include the use of an oligodeoxynucleotide which contains a CpG motif represented by the formula:

5'-$N_1RDCGYTN_2$-3' wherein at least one nucleotide separates consecutive CpGs; RD is selected from the group consisting of GpT, GpG, GpA, ApT and ApA; YT is selected from the group consisting of TpT or CpT; N is any nucleotide and $N_1+N_2$ is from about 0-26 bases, such that the ODN is about 8 to 30 nucleotides in length.

In several embodiments, the methods disclosed herein include the use of an effective amount of at least one K-type CpG ODN, wherein the K-type CpG ODNs include an unmethylated CpG motif that has a sequence represented by the formula:

(SEQ ID NO: 2)
5' $N_1N_2N_3D$-CpG-$WN_4N_5N_6$ 3' wherein the central CpG motif is unmethylated, D is T, G or A, W is A or T, and $N_1$, $N_2$, $N_3$, $N_4$, $N_5$, and $N_6$ are any nucleotides. In one embodiment, D is a T. The K ODN(s) can be 10 to 30 nucleotides in length. A K ODN can include multiple CpG motifs. In some embodiments, at least one nucleotide separates consecutive CpGs; $N_3D$ is selected from the group consisting of GpT, GpG, GpA, ApT and ApA; $WN_4$ is selected from the group consisting of TpT or CpT; N is any nucleotide and $N_1+N_2$ is from about 0-26 bases In one embodiment, $N_1$, and $N_2$ do not contain a CCGG quadmer or more than one CCG or CGG trimer. CpG ODN are also in the range of 8 to 50 bases in length, such as 8 to 30 bases in length, but may be of any size (even many kb long) if sufficient motifs are present. In several examples, the K-type CpG ODN is 10 to 20 nucleotides in length, such as 12 to 18 nucleotides in length. In one embodiment, synthetic oligodeoxynucleotides of this formula do not include a CCGG quadmer or more than one CCG or CGG trimer at or near the 5' and/or 3' terminals and/or the consensus CpG motif is not a palindrome. Other CpG oligodeoxynucleotides can be assayed for efficacy using methods described herein. It should be noted that exemplary K-type CpG ODNs are known in the art, and have been fully described, for example in PCT Publication No. WO 98/18810A1, which is incorporated herein by reference.

Exemplary K ODN are listed below in Table 1:

TABLE 1

| K X | ATAATCGACGTTCAAGCAAG. | (SEQ ID NO: 3) |
|---|---|---|
| K22 | CTCGAGCGTTCTC | (SEQ ID NO: 4) |
| K21 | TCTCGAGCGTTCTC | (SEQ ID NO: 5) |
| K82 | ACTCTGGAGCGTTCTC | (SEQ ID NO: 6) |
| K30 | TGCAGCGTTCTC | (SEQ ID NO: 7) |
| k31 | TCGAGGCTTCTC | (SEQ ID NO: 8) |
| K39 | GTCGGCGTTGAC | (SEQ ID NO: 9) |
| K16 | TCGACTCTCGAGCGTTCTC | (SEQ ID NO: 10) |
| K3 | ATCGACTCTCGAGCGTTCTC | (SEQ ID NO: 11) |
| k23 | TCGAGCGTTCTC | (SEQ ID NO: 12) |
| K40 | GTCGGCGTCGAC | (SEQ ID NO: 13) |
| K34 | GTCGACGTTGAC | (SEQ ID NO: 14) |
| K83 | ACTCTCGAGGGTTCTC | (SEQ ID NO: 15) |
| K19 | ACTCTCGAGCGTTCTC | (SEQ ID NO: 16) |
| K73 | GTCGTCGATGAC | (SEQ ID NO: 17) |
| K46 | GTCGACGCTGAC | (SEQ ID NO: 18) |
| K47 | GTCGACGTCGAC | (SEQ ID NO: 19) |
| K72 | GTCATCGATGCA | (SEQ ID NO: 20) |

TABLE 1-continued

| K37 | GTCAGCGTCGAC | (SEQ ID NO: 21) |
| --- | --- | --- |
| k25 | TCGAGCGTTCT | (SEQ ID NO: 22) |
| K82 | ACTCTGGAGCGTTCTC | (SEQ ID NO: 23) |
| K83 | ACTCTCGAGGGTTCTC | (SEQ ID NO: 24) |
| K84 | ACTCTCGAGCGTTCTA | (SEQ ID NO: 25) |
| K85 | CATCTCGAGCGTTCTC | (SEQ ID NO: 26) |
| K89 | ACTCTTTCGTTCTC | (SEQ ID NO: 27) |
| K109 | TCGAGCGTTCT | (SEQ ID NO: 28) |
| K123 | TCGTTCGTTCTC | (SEQ ID NO: 29) |
| K1555 | GCTAGACGTTAGCGT | (SEQ ID NO: 30) |
| K110 | TCGAGGCTTCTC | (SEQ ID NO: 31) |
| K1826 | TCCATGACGTTCCTGACGTT | (SEQ ID NO: 32) |
| CpG7909 | TCGTCGTTTTGTCGTTTTGTCGTT | (SEQ ID NO: 33) |
| CpG10103 | TCGTCGTTTTACGGCGCCGTGCCG | (SEQ ID NO: 37) |
| CONTROL | | |
| K1612 | TAGAGCTTAGCTTGC | (SEQ ID NO: 34) |
| K1745 | TCCATGAGCTTCCTGAGTCT | (SEQ ID NO: 35) |

A single K-type CpG ODN can be conjugated to a tumor cell for use in the methods disclosed herein. The K-type CpG ODN can be any ODN listed above, including but not limited to K1555 or K3. However, it is also possible to use mixtures of K-type CpG ODNs so that a composition includes the tumor cell of interest conjugated to more than one K-type ODN. Exemplary combinations that can be used to increase an immune response include 1) K3, K19, K110; 2) K19, K23, K123; K3, 3) K110, K123; 4) K3, K23, K123; 5) K3, K19, K123; and 6) K19, K110, K123. Additional exemplary combinations include at least two different K-type CpG ODNs, wherein one of the K-type ODNs is K1555, and/or wherein one of the K-type ODNs is K3.

The K-type CpG ODN can be stabilized. In one embodiment, the stabilized oligodeoxyonucleotide has a modified phosphate backbone. One specific, non-limiting example of a stabilized oligonucleotide has a phosphorothioate modified phosphate backbone (wherein at least one of the phosphate oxygens is replaced by sulfur). Other stabilized oligonucleotides include: nonionic DNA analogs, such as alkyl- and aryl-phosphonates (in which the charged phosphonate oxygen is replaced by an alkyl or aryl group), phosphodiester and alkylphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

D-Type CpG ODN

The present methods can also use D-type CpG ODNs. D-type CpG ODNs (also known as "A" class ODNs) differ both in structure and activity from K-type CpG ODNs (also known as "B" class ODNs) and a third type of ODNs, known as "C" class ODNs. For example, as disclosed herein, D-type CpG ODNs stimulate the release of cytokines from cells of the immune system, and induce the maturation of dendritic cells. In specific, non-limiting examples D-type CpG ODNs stimulate the release or production of IP-10 and IFN-α by monocytes and/or plasmacytoid dendritic cells.

With regard to structure, in one embodiment, a CpG motif in a D-type CpG ODN has been described by the formula:

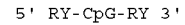

5' RY-CpG-RY 3' wherein the central CpG motif is unmethylated, R is A or G (a purine), and Y is C or T (a pyrimidine). D-type oligonucleotides include an unmethylated CpG dinucleotide. Inversion, replacement or methylation of the CpG reduces or abrogates the activity of the D oligonucleotide.

In one embodiment, a D-type CpG ODN is at least about 16 nucleotides in length and includes a sequence represented by the formula:

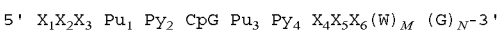

5' $X_1X_2X_3$ $Pu_1$ $Py_2$ CpG $Pu_3$ $Py_4$ $X_4X_5X_6(W)_M$ $(G)_N$-3' wherein the central CpG motif is unmethylated, Pu is a purine nucleotide, Py is a pyrimidine nucleotide, X and W are any nucleotide, M is any integer from 0 to 10, and N is any integer from 4 to 10.

The region $Pu_1$ $Py_2$ CpG $Pu_3$ $Py_4$ is termed the CpG motif. The region $X_1X_2X_3$ is termed the 5' flanking region, and the region $X_4X_5X_6$ is termed the 3' flanking region. If nucleotides are included 5' of $X_1X_2X_3$ in the D ODN, these nucleotides are termed the 5' far-flanking region. Nucleotides 3' of $X_4X_5X_6$ in the D ODN are termed the 3' far-flanking region.

In one specific, non-limiting example, $Py_2$ is a cytosine. In another specific, non-limiting example, $Pu_3$ is a guanidine. In yet another specific, non-limiting example, $Py_2$ is a thymidine and $Pu_3$ is an adenine. In a further specific, non-limiting example, $Pu_1$ is an adenine and $Py_2$ is a tyrosine. In another specific, non-limiting example, $Pu_3$ is an adenine and $Py_4$ is a tyrosine.

In one specific, non-limiting example, N is from about 4 to about 8. In another specific, non-limiting example, N is about 6.

In several embodiments, the D-type CpG ODN is at least about 16 nucleotides in length. For example, the D-type CpG ODNs can be from about 16 to about 50 nucleotides in length, or from about 18 to about 50 nucleotides in length, or from about 18 to about 40 nucleotides in length, or from about 18 to about 30 nucleotides in length. Exemplary D-type CpG ODNs are disclosed below.

D-type CpG ODNs can include modified nucleotides. For example, modified nucleotides can be included to increase the stability of a D-type CpG ODN. Without being bound by theory, because phosphothioate-modified nucleotides confer resistance to exonuclease digestion, the D-type CpG ODNs are "stabilized" by incorporating phosphothioate-modified nucleotides. In one embodiment, the CpG dinucleotide motif and its immediate flanking regions include phosphodiester rather than phosphothioate nucleotides. In one specific, non-limiting example, the sequence $Pu_1$ $Py_2$ CpG $Pu_3$ $Py_4$ includes phosphodiester bases. In another specific, non-limiting example, all of the bases in the sequence $Pu_1$ $Py_2$ CpG $Pu_3$ $Py_4$ are phosphodiester bases. In yet another specific, non-limiting example, $X_1X_2X_3$ and $X_4X_5X_6(W)_m$ $(G)_N$ include phosphodiester bases. In yet another specific, non-limiting example, $X_1X_2X_3$ $Pu_1$ $Py_2$ CpG $Pu_3$ $Py_4X_4X_5X_6(W)_m$ $(G)_N$ (SEQ ID NO: 1) include phosphodiester bases. In further non-limiting examples the sequence $X_1X_2X_3$ includes at most one or at most two phosphothioate bases and/or the sequence $X_4X_5X_6$ includes at most one or at most two phosphothioate bases. In additional non-limiting examples, $X_4X_5X_6(W)_m(G)_N$ includes at least 1, at least 2, at least 3, at least 4, or at least 5 phosphothioate bases. Thus, a D ODN can be a phosphothioate/phosphodiester chimera.

As disclosed herein, any suitable modification can be used to render the D-type CpG ODN resistant to degradation in vivo (for example, via an exo- or endo-nuclease). In one specific, non-limiting example, a modification that renders the oligodeoxynucleotide less susceptible to degradation is the inclusion of nontraditional bases such as inosine and quesine, as well as acetyl-, thio- and similarly modified forms of adenine, cytidine, guanine, thymine, and uridine. Other modified nucleotides include nonionic DNA analogs, such as alkyl or aryl phosphonates (i.e., the charged phosphonate oxygen is replaced with an alkyl or aryl group, as set forth in U.S. Pat. No. 4,469,863), phosphodiesters and alkylphosphotriesters (i.e., the charged oxygen moiety is alkylated, as set forth in U.S. Pat. No. 5,023,243 and European Patent No. 0 092 574). Oligonucleotides containing a diol, such as tetraethyleneglycol or hexaethyleneglycol, at either or both termini, have also been shown to be more resistant to degradation. The D-type oligodeoxynucleotides can also be modified to contain a secondary structure (e.g., stem-loop structure). Without being bound by theory, it is believed that incorporation of a stem-loop structure renders an oligodeoxynucleotide more effective.

In a further embodiment, $Pu_1\ Py_2$ and $Pu_3\ Py_4$ are self-complementary. In another embodiment, $X_1X_2X_3$ and $X_4X_5X_6$ are self-complementary. In yet another embodiment $X_1X_2X_3\ Pu_1\ Py_2$ and $Pu_3\ Py_4\ X_4X_5X_6$ are self-complementary.

Specific non-limiting examples of a D-type CpG ODN wherein $Pu_1\ Py_2$ and $Pu_3\ Py_4$ are self-complementary include, but are not limited to, ATCGAT, ACCGGT, ATCGAC, ACCGAT, GTCGAC, or GCCGGC (wherein the CpG is underlined). Without being bound by theory, the self-complementary base sequences can help to form a stem-loop structure with the CpG dinucleotide at the apex to facilitate immunostimulatory functions. Thus, in one specific, non-limiting example, D-type CpG ODNs wherein $Pu_1\ Py_2$ and $Pu_3\ Py_4$ are self-complementary induce higher levels of IFN-γ production from a cell of the immune system. The self-complementarity need not be limited to $Pu_1\ Py_2$ and $Pu_3\ Py_4$. Thus, in another embodiment, additional bases on each side of the three bases on each side of the CpG-containing hexamer form a self-complementary sequence (see above).

One specific, non-limiting example of a sequence wherein $Pu_1\ Py_2$ and $Pu_3\ Py_4$ are self-complementary but wherein the far-flanking sequences are not self-complementary is GGTGCATCGATACAGGGGGG (DV113, SEQ ID NO: 38, see the Table below)

This oligodeoxynucleotide has a far-flanking region that is not self-complementary and induces high levels of IFN-γ and IFN-α.

Another specific, non-limiting example of a D-type CpG ODN is:

GGTGCGTCGATGCAGGGGGG (DV28, SEQ ID NO: 39, see the Table below)

This D-type CpG ODN is of use for inducing production and/or release of cytokines from immune cells, although it lacks a self-complementary motif.

In one embodiment, the D-type CpG ODNs are at least about 16 nucleotides in length. In a second embodiment, a D-type ODN is at least about 18 nucleotides in length. In another embodiment, a D ODN is from about 16 nucleotides in length to about 100 nucleotides in length. In yet another embodiment, a D-type CpG ODN is from about 16 nucleotides in length to about 50 nucleotides in length. In a further embodiment, a D-type CpG ODN is from about 18 nucleotides in length to about 30 nucleotides in length.

In another embodiment, the D-type CpG ODN is at least 18 nucleotides in length, and at least two G's are included at the 5' end of the molecule, such that the oligodeoxynucleotide includes a sequence represented by the formula:

5' $GGX_1X_2X_3\ Pu_1\ Py_2\ CpG\ Pu_3\ Py_4\ X_4X_5X_6(W)_M\ (G)_N$ 3'.

The D-type CpG ODN can include additional G's at the 5' end of the oligodeoxynucleotide. In one specific example, about 1 or about 2 G's are included at the 5' end of an oligodeoxynucleotide including a sequence as set forth as the above formula.

Examples of a D-type CpG ODN include, but are not limited to the sequence shown in the following table:

TABLE 2

| ODN | SEQUENCE | SEQUENCE IDENTIFIER |
|---|---|---|
| DV113 | GGTGCATCGATACAGGGGGG | (SEQ ID NO: 38) |
| DV28 | GGTGCGTCGATGCAGGGGGG | (SEQ ID NO: 39) |
| DV104 | GGTGCATCGATGCAGGGGGG | (SEQ ID NO: 40) |
| DV19 | GGTGCATCGATGCAGGGGGG | (SEQ ID NO: 40) |
| DV35 | GGTGCATCGATGCAGGGGGG | (SEQ ID NO: 40) |
| DV29 | GGTGCACCGGTGCAGGGGGG | (SEQ ID NO: 41) |
| DV106 | GGTGTGTCGATGCAGGGGGG | (SEQ ID NO: 42) |
| DV116 | TGCATCGATGCAGGGGGG | (SEQ ID NO: 43) |
| DV34 | GGTGCATCGATGCAGGGGGG | (SEQ ID NO: 44) |
| DV102 | GGTGCATCGTTGCAGGGGGG | (SEQ ID NO: 45) |
| DV32 | GGTGCGTCGACGCAGGGGGG | (SEQ ID NO: 46) |
| DV117 | GGTCGATCGATGCACGGGGG | (SEQ ID NO: 47) |
| DV37 | GGTGCATCGATGCAGGGGGG | (SEQ ID NO: 48) |
| DV25 | GGTGCATCGATGCAGGGGGG | (SEQ ID NO: 48) |
| DV30 | GGTGCATCGACGCAGGGGGG | (SEQ ID NO: 49) |
| dv120 | GGTGCATCGATAGGCGGGGG | (SEQ ID NO: 50) |
| DV27 | GGTGCACCGATGCAGGGGGG | (SEQ ID NO: 51) |
| dv119 | CCTGCATCGATGCAGGGGGG | (SEQ ID NO: 52) |
| D142 | GGTATATCGATATAGGGGGG | (SEQ ID NO: 53) |
| d143 | GGTGGATCGATCCAGGGGGG | (SEQ ID NO: 54) |

Underlined bases are phosphodiester. Bold indicates self-complementary sequences. The corresponding sequence identifier is noted. Note that "DV" can also be abbreviated as "D."

Examples of a D-type CpG ODN also include, but are not limited to:

5' NNTGCATCGATGCAGGGGGG 3' (SEQ ID NO: 55)

5' NNTGCACCGGTGCAGGGGGG3' (SEQ ID NO: 56)

-continued

```
                                      (SEQ ID NO: 57)
5'NNTGCGTCGACGCAGGGGGG3', (SEQ ID NO: 58)
5'NNTGCGTCGATGCAGGGGGG3', (SEQ ID NO: 59)
5'NNTGCGCCGGCGCAGGGGGG3', (SEQ ID NO: 60)
5'NNTGCGCCGATGCAGGGGGG3', (SEQ ID NO: 61)
5'NNTGCATCGACGCAGGGGGG3', (SEQ ID NO: 62)
5'NNTGCGTCGGTGCAGGGGGG3',
``` wherein N is any base, or is no base at all. In one specific, non-limiting example, N is a G. Additional exemplary D ODN sequences can be found in U.S. patent application Ser. No. 10/068,160, and in Verthelyi et al., *J. Immunol.* 166:2372-2377, 2001, which are both herein incorporated by reference in their entireties. D-type CpG ODN can be used in combination to induce an immune response. Thus, multiple D-type CpG ODNs can be utilized to induce an immune response. For example, two, three, four, five or more D-type CpG ODNs can be utilized to induce an immune response. In addition, a single ODN can be generated that includes the two or more D-type CpG motifs disclosed herein.

In some embodiments, a single D-type CpG ODN can be conjugated to a tumor cell for use in the methods disclosed herein. The D-type CpG ODN can be any ODN listed above, including but not limited to DV35, DV19, DV28 or DV29. However, it is also possible to use mixtures of D-type CpG ODNs so that a composition includes the tumor cell of interest conjugated to more than one D-type ODN. Thus, DV35, DV19, DV28, DV29 or DV113, or two, three, four or five of these ODNs can be used in combination. In another example, DV35, DV29 and DV19 can be used in combination. Additional exemplary combinations include at least two different D-type CpG ODNs, wherein one of the D-type ODNs is DV35, and/or wherein one of the D-type ODNs is DV28. D-type and K-type ODNs can also be used in combination.

C-type ODNs can also be utilized in the methods disclosed herein. Typically, C class ODNs have a TCGTCG motif at the 5' end and have a CpG motif imbedded in a palindromic sequence.

CpG ODN can be synthesized de novo using any of a number of procedures well known in the art. For example, the oligodeoxynucleotides can be synthesized as set forth in U.S. Pat. No. 6,194,388, which is herein incorporated by reference in its entirety. An ODN can be synthesized using, for example, the B-cyanoethyl phosphoramidite method or nucleoside H-phosphonate method. These chemistries can be performed by a variety of automated oligonucleotide synthesizers available in the market. Alternatively, oligodeoxynucleotides can be prepared from existing nucleic acid sequences (e.g. genomic or cDNA) using known techniques, such as employing restriction enzymes, exonucleases or endonucleases, although this method is less efficient than direct synthesis.

Tumor Cells

In the methods disclosed herein, a CpG ODN (such as a D-type, K-type or C-type ODN) is conjugated to a non-viable tumor cell, such as an apoptotic tumor cell or a necrotic tumor cell, to induce an immune response to the tumor cell. The tumor cell can be from any type of tumor of interest, including a solid or a hematological tumor. Tumor cells include cell lines or primary tumor cells. The cells can be of autologous, allogeneic, syngenic, or xenogenic origin in relation to the subject treated and from the same or from different tissues, organs or cell origin in a species. The tumor cells used in the process can also be mixtures of different tumor cells. In one embodiment the tumor cells can be altered via mutagenesis, infection with pathogenic particles, like viruses, bacteria, fungi, parasites, or via gentechnological methods, thereby introducing novel antigens. In some embodiments the tumor is autologous to the subject being treated with the presently disclosed methods. In one example, the tumor cells are apoptotic tumor cells.

When the tumor cells are derived from tumors or metastases, also including micrometastases, cells can be obtained by surgery, biopsy, fine needle aspiration, or the like. Tumor cell lines can also be utilized in the methods disclosed herein.

The tumor cells can be derived from any possible type of tumors. Examples are skin, breast, brain, cervical carcinomas, testicular carcinomas, head and neck, lung, mediastinum, gastrointestinal tract, genitourinary system, gynaecological system, breast, endocrine system, skin, childhood, unknown primary site or metastatic cancer, a sarcoma of the soft tissue and bone, a mesothelioma, a melanoma, a neoplasm of the central nervous system, a lymphoma, a leukaemia, a paraneoplastic syndrome, a peritoneal carcinomastosis. The tumor cells can be from: head and neck tumor, comprising tumors of the nasal cavity, paranasal sinuses, nasopharynx, oral cavity, oropharynx, larynx, hypopharynx, salivary glands and paragangliomas, a cancer of the lung, comprising non-small cell lung cancer, small cell lung cancer, a cancer of the mediastinum, a cancer of the gastrointestinal tract, comprising cancer of the oesophagus, stomach, pancreas, liver, biliary tree, small intestine, colon, rectum and anal region, a cancer of the genitourinary system, comprising cancer of the kidney, urethra, bladder, prostate, urethra, penis and testis, a gynaecologic cancer, comprising cancer of the cervix, vagina, vulva, uterine body, gestational trophoblastic diseases, ovarian, fallopian tube, peritoneal, a cancer of the breast, a cancer of the endocrine system, comprising a tumor of the thyroid, parathyroid, adrenal cortex, pancreatic endocrine tumors, carcinoid tumor and carcinoid syndrome, multiple endocrine neoplasias, a sarcoma of the soft tissue and bone, a mesothelioma, a cancer of the skin, a melanoma, comprising cutaneous melanomas and intraocular melanomas, a neoplasm of the central nervous system, a cancer of the childhood, comprising retinoblastoma, Wilm's tumor, neurofibromatoses, neuroblastoma, Ewing's sarcoma family of tumors, rhabdomyosarcoma, a lymphoma, comprising non-Hodgkin's lymphomas, cutaneous T-cell lymphomas, primary central nervous system lymphoma, and Hodgkin's disease, a leukaemia, comprising acute leukemias, chronic myelogenous and lymphocytic leukemias, plasma cell neoplasms, a cancer of unknown primary site, a peritoneal carcinomastosis, a Kaposi's sarcoma, AIDS-associated lymphomas, AIDS-associated primary central nervous system lymphoma, AIDS-associated Hodgkin's disease and AIDS-associated anogenital cancers, a metastatic cancer to the liver, metastatic cancer to the bone, malignant pleural and pericardial effusions and malignant ascites. In some examples, the tumor is a lymphoma, breast cancer, colon cancer or lung cancer.

In some examples, non viable cells, such as apoptotic cells or necrotic cells, are prepared from cell lines. In other examples, apoptotic cells are prepared from a subject's tumor biopsy. Thus, in some examples, the methods include preparing a suspension of tumor fragments or of tumor cells from the biopsy, treating the tumor cells or fragments to induce apoptosis, and then conjugating the apoptotic tumor cells to one or more CpG ODNs, such as a K-type ODN, a D-type ODN, a C-type ODN, or any combination thereof.

U.S. Pat. No. 6,703,016, incorporated herein by reference, describes the preparation of apoptotic tumor cells. In one embodiment, a suspension of tumor cells or fragments from a biopsy can be prepared by placing a tumor biopsy in fresh culture medium or buffer with antibiotics; transferring the tissue to fresh sterile medium or buffer; dissecting off non-tumor tissue such as fat, necrotic material and peripheral connective tissues; finely chopping the tumor with crossed scalpels, such as to about 1 mm$^3$; re-suspending the pieces in medium or buffer, allowing the pieces to settle, and removing the supernatant, such as for two to three repetitions; and treating the pieces to induce apoptosis. Collagenase can be used before the treatment of tumor fragments to produce a cell suspension. Mechanical disaggregation can also be used to produce a cell suspension. For example, filtration through about 70 μm nylon membranes can be used to produce a cell suspension. An aliquot can be retained to detect and to quantify apoptosis versus necrosis as described above.

Apoptosis can be induced using a chemical agent, or a ligand or a growth factor. Exemplary chemical agents include butyrate derivatives. stauroporine, sulindac derivatives, inflammatory cytokines, glucocorticoids, antineoplasic nucleoside analogues. In one example, tumor fragments are treated with about 5 to about 10 mM sodium butyrate or with about 0.1 to about 0.5 mM sulindac, in complete medium, such as for about three to about five consecutive days. Apoptotic cells can be collected and stored, such as removed and conserved as 4° C.

Apoptosis can also be induced using a physical agent. In some embodiments, the physical agent is ionization such as γ-irradiation, UV irradiation, heat shock, or stress, such as serum deprivation, or a combination thereof. Ionization can also be utilized, as described, for example in Yamada T., Ohyama H. Int. J. Radiat. Biol. 53:65-75, 1988, which is incorporated herein by reference. In one example, UV irradiation is applied, for example fragments of tumors and/or tumor cells in culture are treated for about 1 to about 5 minutes with a U.V. lamp (220 v, 50 Hz, 180 W), depending on the nature of the tumor cells. In another example, γ-irradiation is utilized to produce apoptotic cells. Tumor fragments are irradiated from 30 gray (Gy) to 150 Gy for 30 minutes, depending on the nature and the origin of tumor cells.

In a further example, heat shock is utilized to produce apoptotic cells. For example, tumor fragments in culture in complete medium are treated for 30 to 60 minutes, at about 40° C. to about 45° C., depending on the nature and the origin of the tumor. Cancer cells or tumor fragments can be treated in suspension, in culture medium. Combinations of agents can be used. One exemplary protocol is about a 2 minute exposure to ultraviolet (U.V.) (such as 220 V, 50 Hz, 180 W) followed by 30 minutes of γ-irradiation at 50 gray for solid tumors. As an example, a combination of a physical and chemical agent can also be used. For example, UV irradiation can be combined with treatment with sodium butyrate, such as to induce apoptosis of cells.

In some examples, the induction of the apoptosis is carried out with sodium butyrate, or sulindac sulfide, such as to produce apoptotic cells from carcinomas and/or leukemias. In additional examples, the induction of the apoptosis is carried out with U.V., such as to produce apoptotic cells from melanomas and leukemia. In further examples, the induction of apoptosis is carried out using heat shock in combination with U.V. irradiation, such as to induce apoptosis of solid tumors. In other examples, the induction of apoptosis is carried out using heat shock in combination with ionization, such as gamma irradiation, such as for leukemic cells. Necrotic cells can be prepared by inducing cell injury, such as by treating cells with chemical compounds such as Concanavalin A (ConA) and cytochalasin D (CytoD), which disrupt the cytoskeleton architecture. Necrosis can also be induced by treating cells with hydrogen peroxide. Necrosis can further be induced by treatment of cytotoxic compounds, including chemotherapeutic agents. In one embodiment, in order to cause death by necrosis, tumor tissue or tumor cells can be frozen. Cryosurgery can induce tissular necrosis by the application of liquid $N_2$ or argon gas. The biologic changes that occur during and after cryosurgery have been studied in vitro and in vivo. Tissue injury and necrosis is induced by cell freezing and by the vascular stasis that develops after thawing.

In another embodiment, tumor tissue or tumor cells are subject to irreversible electroporation. Irreversible electroporation is a tissue ablation technique in which micro to millisecond electrical pulses are delivered to the tissue to produce cell necrosis through irreversible cell membrane permeabilization. In irreversible electroporation, the cellular membranes of the cells between the electrodes are disrupted.

Additional methods for inducing necrosis are described in U.S. Patent Application Publication No. 2008/0112975, which is incorporated herein by reference. Necrosis includes a cell death by a variety of methods including cryoablation, irreversible electroporation, chemotherapy, radiation therapy, ultrasound therapy, ethanol chemoablation, microwave thermal ablation, radio frequency energy or a combination thereof.

Conjugation Methods

In several embodiments, disuccinimidyl suberate (DSS) or bis[sulfosuccinimidyl]suberate (BS3), is used to cross-link cells to CpG ODN. DSS is a water-insoluble, homobifunctional N-hydroxysuccinimide ester (NHS ester), and BS3 is its water-soluble analog. NHS esters react efficiently with primary amino groups (—NH2) in pH 7-9 buffers to form stable amide bonds. The reaction results in the release of N-hydroxysuccinimide. Proteins, including antibodies, generally have several primary amines in the side chain of lysine (K) residues and the N-terminus of each polypeptide that are available as targets for NHS-ester reagents. The water-soluble and insoluble forms of NHS-esters have essentially identical reactivity toward primary amines. BS3 is supplied as a sodium salt and is water-soluble up to 10 mM. DSS is hydrophobic and dissolved in an organic solvent such asdimethyl sulfoxide (DMSO) or dimethyl formamide (DMF) then added to the aqueous reaction mixture. DSS does not possess a charged group and is lipophilic and membrane-permeable, which makes it useful for intracellular and intramembrane conjugations. Water-soluble BS3 possess a charged group and is useful for cell-surface protein crosslinking. Thus, disuccinimidyl suberate (DSS) or bis[sulfosuccinimidyl]suberate (BS3), is used to cross-link non-viable cells, such as apoptotic cells or necrotic cells to CpG ODN.

However, any suitable method can be used to conjugate a K-type-CpG ODN, D-type CpG ODN, C-type CpG ODN, or a combination thereof to a tumor cell. In one embodiment the CpG ODN is conjugated to a non-viable tumor cell, such as an apoptotic tumor cell, using crosslinkers such as maleimide crosslinkers (Table 1), which possess two different reactive groups that allow for conjugations with specific sites on proteins. Sulfo-EMCS (aliphatic maleimide linker) and sulfo-SMPB (aromatic maleimide linker) heterobifuntional crosslinkers (see Table 1 below and associated structures) (Myers et al, J. Immunol. Methods (1989) 121:129-142) are can be used.

TABLE 3

Maleimide Heterobifunctional Crosslinkers

| | Chemical Name |
|---|---|
| SMCC/Sulfo-SMCC | Sulfosuccinimidyl 4-[N-maleimidomethyl] cyclohexane-1-carboxylate |
| EMCS/Sulfo-EMCS | N-[ε-Maleimidocaproyloxy]sulfosuccinimide ester |
| Sulfo-MBS | m-Maleimidobenzoyl-N-hydroxysulfosuccinimide ester |
| Sulfo-KMUS | N-[κ-Maleimidoundecanoyloxy]sulfosuccinimide ester |
| BMPH | N-[β-Maleimidopropionic acid] Hydrazide•TFA |
| BMPS | N-[β-Maleimidopropyloxy] succinimide ester |
| GMBS/Sulfo-GMBS | N-[γ-Maleimidobutyryloxy]sulfosuccinimide ester |
| SMPB/Sulfo-SMPB | Sulfosuccinimidyl 4-[p-maleimidophenyl]butyrate |
| SMPH | Succinimidyl 4-[p-maleimidophenyl]butyrate |

Sulfo-EMCS

Sulfo-SMPB

Typically, maleimide crosslinkers are water-soluble analogues and consist of an N-hydroxysuccinimide (NHS) ester and a maleimide group connected with a spacer arm which limits steric hindrance. NHS esters will react with primary amines of a protein on the apoptotic cell, and after purification, the maleimide group will react with the thio functional group of a CpG ODN, such as a K-type CpG ODN, a D-type CpG ODN, or a C-type CpG ODN. The apoptotic cell conjugated with the various crosslinkers to CpG ODN will be compared for differences in yields and CpG ODN activity.

The non-viable cells, such as apoptotic cells or necrotic cells, can be cross-linked to a CpG ODN according to the standard procedures (e.g., chemical manufacturer's instructions) or other procedures such as those described (Khawli et al. Cancer Biother & Radiopharm. 11: 203-215, 1996; Sharif et al., Q J. Nucl. Med. 42:242-249, 1998). Briefly, proteins on a cell are derivatized with conjugation buffer (0.05M PBS, 3 mM EDTA, pH 7.5) for 30 minutes at room temperature with different molar ratios of the maleimide crosslinking agent to proteins on the cell using water-soluble analogues. Excess crosslinking reagent is removed by Sephadex G-25 column chromatography. To a solution of 3'-thiol-modified CpG ODN (such as K-type CpG ODN or a D-type CpG ODN), 0.1M dithiothreitol (DTT/pH 8.3-8.5) is added for 30 minutes at room temperature. Excess DTT is removed by desalting on a Sephadex G-10 column equilibrated with the conjugation buffer as above. Immediately following purification, derivatized cells are reacted with different molar ratios of 3'-thiol CpG ODN to antibody for 1-2 hours at room temperature. Free CpG ODN is separated from conjugated CpG ODN by size exclusion. The different fractions are concentrated, filtered, and further analyzed by sodium dodecylsulfate-polyacrylamide gel electrophoresis (SDS-PAGE) and by high-pressure liquid chromatography (HPLC) to determine purity.

The number of CpG ODN molecules per cell can be determined spectrophotometrically and calculated as $OD_{260}/OD_{280}$ ratio as described by Ngo and Oliva (protocol according to TriLink BioTechnologies, La Jolla, Calif.). Alternatively, the CpG ODN can be labeled, such as with a fluorescent label, and the amount of the label associated with the cells can be determined.

In vitro assays using splenocytes and macrophages or other types of cells that express receptors may be used to demonstrate that the CpG ODN portion of the invention conjugate remains active after chemical conjugation. For example, in vitro assays using mouse splenocytes or J7-74 and J77743 A mouse macrophages can be performed (Kandimilla et al., Bioconjug. Chem. (2002) 13:966-974). Briefly, splenocytes or J7-74 or J77743A cells are plated in 24 well dishes using $10^6$ cells/ml. CpG ODN alone (positive control) and the CpG conjugate is added at different equimolar concentrations (0.03 to 10.0 μg/ml) to the cell cultures. The cells are incubated at 37° C. for 24 hours and the supernatants collected for ELISA determination of secreted cytokines such as IL-12, IL-6, IFN-γ, and other pertinent cytokines and chemokines. Sandwich ELISAs are commercially available for such cytokines (see e.g., R&D Sciences, Minneapolis, Minn.).

Activity of the disclosed conjugates of CpG ODN and apoptotic cells can be demonstrated in tumor animal models, such as tumor-bearing nude or BALB/c mice. Studies may include in vivo determination of pharmacokinetic clearance, biodistribution, imaging, and toxicity. In addition, the ability of the conjugates to induce a B cell response can be evaluated, such as by assessing the presence of antibodies that specifically bind the tumor cells. Furthermore, the anti-tumor activity of each reagent can be studied in tumor-bearing mice by assessing their effects on tumor growth (tumor volume, survival times, number and size of metastases) and tumor morphology. Examples of these assays are described in the Examples section below.

Pharmaceutical Compositions and Methods of Use

Methods are disclosed herein for producing an immune response to a tumor in a subject. Methods are disclosed herein for preventing formation of a tumor, treating a tumor, or reducing the risk of developing a tumor in a subject. In some embodiments, methods are disclosed herein for preventing conversion of a benign to a malignant lesion, or preventing metastasis in a subject. In some examples, the methods reduce a symptom of the tumor in the subject.

Generally, the methods include selecting a subject having a tumor or at risk of developing a tumor, and administering to the subject a therapeutically effective amount of non-viable tumor cells, such as apoptotic tumor cells or necrotic cells, conjugated to one or more CpG ODN, such as K-type CpG ODN, D-type CpG ODN, C-type CpG ODN, or a combination thereof, thereby producing an immune response to the tumor, treating the tumor, preventing the formation of a tumor, reducing the risk of developing a tumor, or preventing the conversion of a benign to a malignant tumor.

The methods disclosed herein include selecting a subject in need of treatment for the condition (for example, a subject with a tumor or a subject at risk of developing a tumor, such as subject exposed to a carcinogen), and administering to the subject a therapeutically effective amount of one or more non-viable tumor cells, such as apoptotic tumor cells or necrotic tumor cells, conjugated to a CpG ODN, such as K-type CpG ODN, D-type CpG ODN, C-type CpG ODN, or a combination thereof. In some examples, more than one CpG ODN is utilized, such as two, three, four or five CpG ODN. These ODNs can be of the same type or can be different types. Additional agents can also be administered to the subject of interest, such as, but not limited to, chemotherapeutic agents.

In several embodiments, the present disclosure is further directed to methods for decreasing the risk of developing a tumor in a subject exposed to a carcinogen, or preventing or delaying the development of a tumor.

The tumor can be any tumor of interest, including, but not limited to, lymphoma, breast cancer, lung cancer and colon cancer. The tumor can be benign or malignant. Additional examples are skin, breast, brain, cervical carcinomas, testicular carcinomas, head and neck, lung, mediastinum, gastrointestinal tract, genitourinary system, gynaecological system, breast, endocrine system, skin, childhood, unknown primary site or metastatic cancer, a sarcoma of the soft tissue and bone, a mesothelioma, a melanoma, a neoplasm of the central nervous system, a lymphoma, a leukemia, a paraneoplastic syndrome, a peritoneal carcinomastosis. The tumor cells can be from: head and neck tumor, comprising tumors of the nasal cavity, paranasal sinuses, nasopharynx, oral cavity, oropharynx, larynx, hypopharynx, salivary glands and paragangliomas, a cancer of the lung, comprising non-small cell lung cancer, small cell lung cancer, a cancer of the mediastinum, a cancer of the gastrointestinal tract, comprising cancer of the oesophagus, stomach, pancreas, liver, biliary tree, small intestine, colon, rectum and anal region, a cancer of the genitourinary system, comprising cancer of the kidney, urethra, bladder, prostate, urethra, penis and testis, a gynaecologic cancer, comprising cancer of the cervix, vagina, vulva, uterine body, gestational trophoblastic diseases, ovarian, fallopian tube, peritoneal, a cancer of the breast, a cancer of the endocrine system, comprising a tumor of the thyroid, parathyroid, adrenal cortex, pancreatic endocrine tumors, carcinoid tumor and carcinoid syndrome, multiple endocrine neoplasias, a sarcoma of the soft tissue and bone, a mesothelioma, a cancer of the skin, a melanoma, comprising cutaneous melanomas and intraocular melanomas, a neoplasm of the central nervous system, a cancer of the childhood, comprising retinoblastoma, Wilm's tumor, neurofibromatoses, neuroblastoma, Ewing's sarcoma family of tumors, rhabdomyosarcoma, a lymphoma, comprising non-Hodgkin's lymphomas, cutaneous T-cell lymphomas, primary central nervous system lymphoma, and Hodgkin's disease, a leukaemia, comprising acute leukemias, chronic myelogenous and lymphocytic leukemias, plasma cell neoplasms, a cancer of unknown primary site, a peritoneal carcinomastosis, a Kaposi's sarcoma, AIDS-associated lymphomas, AIDS-associated primary central nervous system lymphoma, AIDS-associated Hodgkin's disease and AIDS-associated anogenital cancers, a metastatic cancer to the liver, metastatic cancer to the bone, malignant pleural and pericardial effusions and malignant ascites. In some examples, the tumor is a lymphoma, breast cancer, colon cancer, prostate cancer or lung cancer.

Treatment of the conditions described herein are generally initiated after the development of a condition described herein, or after the initiation of a precursor condition (such as dysplasia or development of a benign tumor). Treatment can be initiated at the early stages of cancer, for instance, can be initiated before a subject manifests symptoms of a condition, such as during a stage I diagnosis or at the time dysplasia is diagnosed. However, treatment can be initiated during any stage of the disease, such as but not limited to stage I, stage II, stage III and stage IV cancers. In some examples, such as for breast cancer, treatment can be initiated before or during exposure to an agent that damages DNA, such as a result of an exposure to a carcinogen or UV light, oxidative stress, alkylation damage and deamination. Treatment prior to the development of the condition, such as treatment upon detecting dysplasia or an early (benign) precursor condition, is referred to herein as treatment of a subject that is "at risk" of developing the condition. In some embodiments, administration of a composition can be performed during or after the occurrence of the conditions described herein.

Treatment initiated after the development of a condition, such as malignant cancer, may result in decreasing the severity of the symptoms of one of the conditions, or completely removing the symptoms, or reducing metastasis, tumor volume or number of tumors. Treatment can also include increasing the immune response to the tumor, such as by increasing the humoral response. In one example, there is an increase in antibodies that specifically bind the tumor. In some examples, treatment is administered to these subjects with a benign tumor that can convert into a malignant or even metastatic lesion. However, in other examples, treatment is administered to any subject diagnosed with cancer. Exemplary tumors are lymphomas, cervical carcinoma, prostate cancers, breast cancers, colon cancers or lung cancers In one aspect of the disclosure, the formation of tumors, such as metastasis, are delayed, prevented or decreased. In another aspect, the size of the primary tumor is decreased. In a further aspect, a symptom of the tumor is decreased. In yet another aspect, tumor volume is decreased.

The presence of a tumor can be determined by methods known in the art, and typically include cytological and morphological evaluation. The cells can be in vivo or ex vivo, including cells obtained from a biopsy.

The compositions described herein may be formulated in a variety of ways for administration to a subject to induce an immune response to a tumor, or to delay, prevent, reduce the risk of developing, or treat, any tumor of interest. The compositions described herein can also be formulated for application such that they prevent metastasis of an initial lesion.

In some examples, the methods are for the treatment of a subject with a tumor. In some embodiments, a suspension of cells is produced from the tumor. The tumor can be autologous, such as from a biopsy sample. However, the tumor can also be heterologous, such as from a cell line or another individual. The tumor cells are treated to form non-viable tumor cells, such as necrotic or apoptotic tumor cells, and the cells are conjugated to one or more CpG ODN, such as K-type CpG ODN, D-type CpG ODN, C-type CpG ODN, or a combination thereof. A therapeutically effective amount of the apoptotic tumor cells are then administered to the subject, such as to induce an immune response. The immune response can be measured, such as by measuring antibody titer, tumor volume can be measured, the number of metastatic lesions can be measured, or a symptom of a tumor can be measured. A therapeutically effective dose of the apoptotic tumor cells conjugated to the one or more CpG ODN increases the immune response, such as the antibody titer, decreases tumor volume, decreases the number and/or size of metastases, and/or decreases one or more symptoms of the tumor.

Pharmaceutical compositions can include a non-viable tumor cell, such as an apoptotic tumor cell or a necrotic tumor cell, conjugated to one or more CpG ODN, as described herein as an active ingredient. These compositions can also include apoptotic and/or necrotic tumor cells conjugated to one or more CpG ODN, such as K-type CpG ODN, D-type CpG ODN, C-type CpG ODN, or a combination thereof, and an additional agent, such as an additional chemotherapeutic agent.

Pharmaceutical compositions are thus provided for both local use and for systemic (such as oral or intravenous) use. Therefore, the disclosure includes within its scope pharmaceutical compositions comprising a non-viable tumor cell, such as an apoptotic tumor cell or a necrotic tumor cell, conjugated to at least one CpG ODN formulated for use in human or veterinary medicine. While the ODN will typically be used to treat human subjects they may also be used to treat similar or identical diseases in other vertebrates, such as other primates, dogs, cats, horses, and cows. A suitable administration format may best be determined by a medical practitioner for each subject individually. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42: 2S, 1988. The dosage form of the pharmaceutical composition will be determined by the mode of administration chosen.

When locally administered into cells in an affected area or a tissue of interest, the non-viable tumor cell, such as an apoptotic tumor cell or a necrotic tumor cell, conjugated to one or more CpG ODNs, such as K-type CpG ODN, D-type CpG ODN, C-type CpG ODN, or a combination thereof can be administered in a composition that contains a synthetic or natural hydrophilic polymer as the carrier. Examples of such polymers include hydroxypropyl cellulose and polyethylene glycol. Apoptotic cells conjugated to one or more CpG ODN can be mixed with a hydrophilic polymer in an appropriate solvent. The solvent is then removed by methods such as air-drying, and the remainder is then shaped into a desired form (for example, a sheet) and applied to the target site. Formulations containing such hydrophilic polymers keep well as they have a low water-content. At the time of use, they absorb water, becoming gels that also store well. In the case of sheets, the firmness can be adjusted by mixing a polyhydric alcohol with a hydrophilic polymer similar to those above, such as cellulose, starch and its derivatives, or synthetic polymeric compounds. Hydrophilic sheets thus formed can be used.

The non-viable tumor cells, such as apoptotic tumor cells or necrotic tumor cells, conjugated to one or more CpG ODN can be formulated for administration by inhalation, such as, but not limited to, formulations for the treatment of lung or esophageal cancer. Inhalational preparations include aerosols, particulates, and the like. In general, the goal for particle size for inhalation is about 1 μm or less in order that the pharmaceutical reaches the alveolar region of the lung for absorption. However, the particle size can be modified to adjust the region of disposition in the lung. Thus, larger particles can be utilized (such as about 1 to about 5 μm in diameter) to achieve deposition in the respiratory bronchioles and air spaces. In addition, oral formulations may be liquid (e.g., syrups, solutions, or suspensions), or solid (e.g., powders, pills, tablets, or capsules).

For administration by inhalation, the non-viable tumor cells, such as apoptotic tumor cells or necrotic tumor cells, conjugated to one or more CpG ODN can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

The compositions or pharmaceutical compositions including non-viable tumor cells, such as apoptotic tumor cells or necrotic tumor cells, conjugated to one or more CpG ODN also can be administered by any route, including parenteral administration, for example, intravenous, intraperitoneal, intramuscular, intraperitoneal, intrasternal, or intraarticular injection or infusion, or by sublingual, oral, topical, intranasal, or transmucosal administration, or by pulmonary inhalation. When ODNs are provided as parenteral compositions, e.g. for injection or infusion, they are generally suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate-acetic acid buffers. A form of repository or "depot" slow release preparation may be used so that therapeutically effective amounts of the preparation are delivered into the bloodstream over many hours or days following transdermal injection or delivery.

Non-viable tumor cells (including apoptotic and necrotic tumor cells) conjugated to one or more CpG ODN are also suitably administered by sustained-release systems. Suitable examples of sustained-release compositions include suitable polymeric materials (such as, for example, semi-permeable polymer matrices in the form of shaped articles, e.g., films, or mirocapsules), suitable hydrophobic materials (such as, for example, an emulsion in an acceptable oil) or ion exchange resins, and sparingly soluble derivatives (such as, for example, a sparingly soluble salt). Sustained-release apoptotic tumor cells conjugated to one or more ODNs may be administered orally, rectally, parenterally, intracisternally, intravaginally, intraperitoneally, topically (as by powders, ointments, gels, drops or transdermal patch), bucally, or as an oral or nasal spray.

Preparations for administration can be suitably formulated to give controlled release of non-viable tumor cells (such as apoptotic or necrotic tumor cells) conjugated to one or more CpG ODN, such as K-type CpG ODN, D-type CpG ODN, C-type CpG ODN, or a combination thereof, over an extended period of time. For example, the pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features which allow a controlled release of the active substance. See U.S. Pat. No. 5,700,486.

The pharmaceutically acceptable carriers and excipients useful in this invention are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

Generally, the formulations are prepared by contacting the non-viable tumor cells, such as apoptotic tumor cells or necrotic tumor cells, conjugated to one or more CpG ODN each uniformly and intimately with liquid carriers or finely divided solid carriers or both. Then, if necessary, the product is shaped into the desired formulation. Optionally, the carrier is a parenteral carrier, and in some embodiments it is a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The pharmaceutical compositions that comprise non-viable tumor cells, such as apoptotic tumor cells or necrotic tumor cells, conjugated to one or more CpG ODN, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated. Multiple treatments are envisioned, such as over defined intervals of time, such as daily, bi-weekly, weekly, bi-monthly or monthly, such that chronic administration is achieved. As disclosed herein, therapeutically effective amounts of non-viable tumor cells conjugated to one or more CpG ODN, including K-type CpG ODN, D-type CpG ODN, C-type CpG ODN, and combinations thereof, are of use for inducing an immune response to the tumor cells, preventing formation of a tumor, treating a tumor, preventing conversion of a benign to a malignant lesion, decreasing the risk of developing a tumor, or preventing metastasis. Administration may begin whenever the suppression or prevention of disease is desired, for example, at a certain age of a subject, or prior to an environmental exposure.

The therapeutically effective amount of non-viable tumor cells, such as apoptotic tumor cells or necrotic tumor cells, conjugated to one or more CpG ODN will be dependent on the CpG ODN(s) utilized, the subject being treated, the severity and type of the affliction, and the manner of administration. For example, a therapeutically effective amount of apoptotic tumor cells conjugated to one or more CpG ODN vary from about 0.01 µg per kilogram (kg) body weight to about 1 g per kg body weight, such as about 1 µg to about 5 mg per kg body weight, or about 5 µg to about 1 mg per kg body weight. The exact dose is readily determined by one of skill in the art based on the potency of the specific compound (such as the ODN utilized), the age, weight, sex and physiological condition of the subject. In one example, about 1 to about 100 µg of ODN is administered, conjugated to about $10^6$ tumor cells. In another example, about 2 to about 50 µg of ODN is conjugated to about $10^6$ tumor cells. In a further example, about 5 to about 20 µg of ODN is conjugated to about $10^6$ tumor cells. In a further example, about 5 to about 15 µg of ODN is conjugated to about $10^6$ tumor cells. In this context, about indicates within 10 to 20% of the value.

In several embodiments, about $10^6$ to about $10^{10}$ of the conjugated tumor cells are administered to a subject, such as about $10^7$ to about $10^{10}$ conjugated cells. Thus, in several examples, $10^6$, $10^7$, $10^8$, $10^9$ or $10^{10}$ conjugated cells are administered to the subject. In additional examples, $2\times10^6$, $2\times10^7$, $2\times10^8$, $2\times10^9$ or $2\times10^{10}$ conjugated cells are administered. In other examples, $5\times10^6$, $5\times10^7$, $5\times10^8$, $5\times10^9$ or $5\times10^{10}$ conjugated cells are administered to the subject.

A therapeutically effective amount of non-viable tumor cells, such as apoptotic tumor cells or necrotic tumor cells, conjugated to one or more K-type, D-type, and/or C-type CpG ODN can be administered with a therapeutically effective amount of another agent, such as a cytokine, a chemokine, or a chemotherapeutic agent. In one example, for the prevention and treatment of cancer, such as lung cancer, colon cancer or prostate cancer, the non-viable tumor cell conjugated to one or more K-type CpG ODN can be used with surgical treatment, or with another therapeutic agent, such as a cytokine, including interleukin-2 (IL-2), granulocyte macrophage colony stimulating factor (GM-CSF), or interferon, such as interferon (IFN). In one example, this administration is sequential. In other examples, this administration is simultaneous. Examples of chemotherapeutic agents are alkylating agents, antimetabolites, natural products, or hormones and their antagonists. Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine). Examples of antimetabolites include folic acid analogs (such as methotrexate), pyrimidine analogs (such as 5-FU or cytarabine), and purine analogs, such as mercaptopurine or thioguanine. Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Examples of miscellaneous agents include platinum coordination complexes (such as cis-diaminedichloroplatinum II also known as cisplatin), substituted ureas (such as hydroxyurea), methyl hydrazine derivatives (such as procarbazine), and adrenocrotical suppressants (such as mitotane and aminoglutethimide). Examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol. Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

This disclosure is illustrated by the following non-limiting examples:

EXAMPLES

The primary goal of cancer immunotherapy is to eradicate tumor cells by inducing a protective immune response against tumor-associated antigens (TAA). While whole tumor cells provide a comprehensive source of TAA (eliminating the need to identify individual antigens that may vary between tumors and patients), they generally have been shown to be poorly immunogenic.

The conjugation of immunostimulatory CpG oligodeoxynucleotides (ODN) to apoptotic tumor cells is described herein. The CpG-tumor cell conjugates were highly immunogenic. CpG conjugation enhanced the uptake of target cells by DCs, triggered the up-regulation of co-stimulatory molecules, and promoted the production of immunomodulatory cytokines (such as IL-12). Vaccination with CpG-conjugated tumor cells stimulated the expansion of tumor-specific CTL that reduced the growth of established tumors and metastases.

Example 1

Materials and Methods

Animals and Tumor Cell Lines:

C57BL/6 mice were obtained from the National Cancer Institute (Frederick, Md.) and studied at 6-10 weeks of age. OT-1 mice carrying ovalbumin (OVA)-T cell receptor transgenic T cells specific for the H-2 Kb-restricted CTL epitope on a RAG-1-/- background were obtained from The Jackson Laboratory. The following cell lines were purchased from American Type Culture collection (Manassas, Va.): E.G7, which is a $CD8^+$ T cell line derived from the EL-4 thymoma that had been transfected to express ovalbumin (Moore et al., Cell 1988; 54:777-785); TC-1, which is a lung epithelial tumor cell line that expresses the E7 oncoprotein from Human papilloma virus 16 (Chu et al., Cell Stress Chaperones 2000; 5:401-405); TRAMP C-1, which is a transgenic adenocarcinoma derived from a prostate tumor that arose in a TRAMP mouse (Foster Foster et al., Cancer Res 1997; 57:3325-3330) and 4.T1, which is a metastatic breast cancer cell line (Pulaski et al., Cancer Res 2000; 60:2710-2715).

Reagents:

Phosphorothioate ODNs and $NH_2$ and fluorescein isothiocyanate (FITC) labeled ODNs were synthesized at the Core Facility of the Center for Biologics Evaluation and Research, Food and Drug Administration (Bethesda, Md.). The following ODNs were used: CpG ODN 1826 (TCCATGACGTTCCTGACGTT, SEQ ID NO: 32), control ODN 1745 (TCCATGAGCTTCCTGAGTCT, SEQ ID NO: 35). All ODN were free of detectable protein or endotoxin contamination. Endotoxin contamination was assessed using the Limulus amebocyte cell lysate assay (Cambrex Bio Science, Walkersville, Md., sensitivity 0.1 units of endotoxin/mg) and protein contamination using the Pierce bicinchoninic acid protein assay kit (Thermo scientific, Rockford, Ill., sensitivity 2.5 ug/ml).

Chemical Conjugation of ODN to Cells:

The apoptosis of tumor cells was induced by adding 50 ug/ml of mitomycin C (Sigma-aldrich, St. Louis, Mo.) to growing cultures for 16 hours at 37° in a 5% $CO_2$ in air incubator. Tumor cells treated with 15,000 rads could be substituted with similar effect. Both treatments led to the apoptosis of >90% of cells (as confirmed by annexin V and propidium iodide staining) within 24 hr. Mitomycin C or irradiated tumor cells never produced tumors when transferred into naive recipients.

After the induction of apoptosis, cells were washed and incubated with 0.5-1 mg/ml of amino modified CpG or control ODN in PBS for 1 hourr at 4° C., followed by 5 uM of BS3 (Thermo Scientific), a cell impermeable cross linking agent for 1 hr. Under these conditions, 70-80% of the ODN bound to the surface of apoptotic cancer cell lines (established by monitoring the loss of free ODN from cell supernatants), yielding a vaccine in which 10-20 ug of ODN was incorporated into each dose of vaccine. Unbound ODN was removed completely by centrifugation.

CFSE Labeling:

Tumor cells were labeled with carboxyfluorescein succinimidyl ester (CFSE) as recommended by the manufacturer. Briefly, $2\times10^6$ tumor cells in PBS were incubated with 0.5 uM CFSE (Invitrogen, Carlsbad, Calif.) for 10 min. at 37°. After incubation, the cells were washed twice with PBS.

Preparation of BMDCs:

Bone marrow derived dendritic cells (BMDCs) were prepared from C57Bl/6 mice as previously described (Shirota et al., J Immunol 2001; 167:66-74). Briefly, $10^6$ cells obtained from the femur were seeded into a 100 mm Petri dish in 10 ml of RPMI supplemented with 10% fetal calf serum (FCS) and 20 ng/ml GM-CSF (BD PharMingen, San Diego, Calif.). Medium was replaced on day 3, and the cells harvested on day 7 by treatment with Tripsin/EDTA for 5 min. These cells were analyzed by FACS and found to be >90% $CD11c^+$.

Enrichment of Splenic DCs:

Spleens were removed under sterile conditions, cut into fragments, and incubated with RPMI 1640 supplemented with 1 mg/ml collagenase D (Boehringer Mannheim, Indianapolis, Ind.) for 30 min at 37°. After washing, the cells were layered onto 50% Percoll and centrifuged for 20 min at 2000 rpm. The interface was recovered and used as the DCs-enriched fraction for flow cytometry analysis (Shirota et al., supra). This procedure enriched CD11c cells from 2% prior to treatment to 25-30% after the enrichment.

In vivo tumor studies: Individual mice were immunized intraperitoneally (i.p.) with one of several candidate tumor cell vaccines prepared by chemically conjugating CpG ODN to apoptotic tumor cells. Mice were challenged either pre- or post-immunization with viable tumor cells subcutaneously (s.c.) (the number of cells varied with the tumor type as described in the figure legends). Tumor growth curves were generated using 5-10 mice per group and all results were derived by combining data from 2-3 independent experiments. Tumor size was calculated by the formula: (length×width×height)/2. Any animal whose tumor exceeded a diameter of 2.0 cm was immediately euthanized as per ACUC protocol.

To deplete $CD4^+$ vs $CD8^+$ T cell subsets, mice were injected i.p. with 25 ul ascites of rat anti-mouse $CD4^+$ (L3/T4) or mouse anti-mouse $CD8^+$ (Ly2.2) Abs from Cedarlane labs (Burlington, N.C.) on day −2, 0 and then twice per week post tumor implantation.

The post-surgical model of metastatic 4T1 mammary carcinoma was described previously (Pulaski et al., Cancer Res 2000; 60:2710-2715). Briefly, mice were challenged s.c. in the flank with $5\times10^4$ 4T1 cells. Once the primary tumor reached a diameter of >10 mm (typically by day 14-17), it was surgically removed (including a 5 mm margin) and the mice monitored for survival.

Flow Cytometry:

Cells were washed with PBS, fixed in 4% paraformaldehyde for 10 minutes, and stained with anti-CD11c, -CD40, -CD69 or -CD86 Abs for 30 minutes at 4°. All Abs used were obtained from BD Pharmingen (San Diego, Calif.) while the PE conjugated SIINFEKL (SEQ ID NO: 36)/Kb pentamer was obtained from Proimmune (Bradenton, Fla.). Stained cells were washed, re-suspended in PBS/0.1% BSA plus azide, and analyzed by FACSort (BD Biosciences). For detection of intracytoplasmic IL-12, BMDCs were co-cultured with ODN conjugated cells and brefeldin A (Sigma-Aldrich) added 4 hours later for 4 hours. After staining with anti- CD11c, the cells were treated with cell permeabilization solution (BD Pharmingen) and then stained with anti-IL-12 antibody (Ab).

ELISpot Assay:

Single cell suspensions were prepared from whole spleen. $1.5-3.0\times10^5$ splenocytes/well were stimulated for 12-14 hr with 100 ug/ml of OVA (Sigma Chemical Co., St. Louis, Mo.) or E7 peptide (0.1 ug/ml) or apoptotic tumor cells in 96 well Immulon II plates (Millipore, Billerica, Mass.) previously coated with monoclonal rat anti-IFNg Ab (R4-6A2) (BD Biosciences). The plates were washed and treated with biotinylated polyclonal goat anti-IFNg Ab (R & D systems, MN) followed by streptavidin alkaline phosphatase. Spots were visualized by the addition of a 5-bromo-4-chloro-3-indolyl phosphatase solution (Sigma Aldrich) in low melt agarose (Sigma Aldrich) and counted manually under X40 magnification. The number of cytokine secreting cells was determined by a single blind reader, and all data was generated by analyzing three separate wells per sample.

Statistical Analysis:

A two-sided unpaired Student's t test was used to analyze tumor growth and cellular responses. The Wilcoxon test of Kaplan-Meier plots was used to analyze differences in animal survival. P values <0.05 were considered to be statistically significant.

Example 2

CpG Conjugated Tumor Cells Reduce the Growth of Established Tumors

Therapeutically useful vaccines can significantly inhibit the growth of primary tumors that have reached clinically detectable size and/or prevent their metastatic spread. Initial studies examined the effect of CpG-conjugated apoptotic tumor cell vaccines on the in vivo growth of TRAMP C-1 cells. These tumor cells grow to form detectable masses (5-8 mm in diameter) 5-6 weeks after being injected into the flank of syngeneic C57Bl/6 mice.

The cell impermeable cross-linking agent BS3 was used to covalently bind CpG or control ODN to the surface of mitomycin C treated TRAMP C-1 cells (hereafter referred to as CpG-TRAMP). Preliminary studies established that mitomycin C induced tumor cells to undergo apoptosis, that treated cells could not form tumors in naive mice, and that the conjugation procedure bound 10-20 ug of ODN per dose of vaccine to the cell surface. Substituting other methods for inducing apoptosis, such as irradiation, also produced tumor cell vaccines that were immunogenic when conjugated to CpG ODN.

Five to six weeks after injecting mice with TRAMP C-1 cells (once the tumors had reached clinically detectable size), mice were immunized and boosted with CpG-TRAMP. As shown in FIG. 1A, these animals generated strong cellular responses against the tumor as manifest by a significant expansion in the number of T cells responding to tumor re-stimulation ex vivo (p.<0.01, FIG. 1A).

This vaccination strategy significantly slowed the growth of established TRAMP C-1 tumors in vivo (p<0.01 vs unvaccinated animals, FIG. 1B). Even greater protection was achieved when CpG-TRAMP was administered weekly for one month (FIG. 1C). Vaccination with CpG ODN alone, unconjugated tumor cells, apoptotic TRAMP C-1 cells conjugated to control ODN (control-TRAMP) or apoptotic TRAMP C-1 cells mixed with but not conjugated to CpG ODN (CpG+TRAMP) were ineffective at slowing tumor growth.

Example 3

CpG Conjugated Tumor Cells Prevent Metastatic Spread Following Surgical Resection of Primary Tumors As primary tumors increase in size and/or metastasize, cancer monotherapy is typically replaced by a combination of surgery, radiation, chemo- and/or immuno-therapy. Thus, the ability of CpG-conjugated tumor cell vaccines to prevent metastasis after surgical removal of primary tumors was evaluated.

Figure 2:
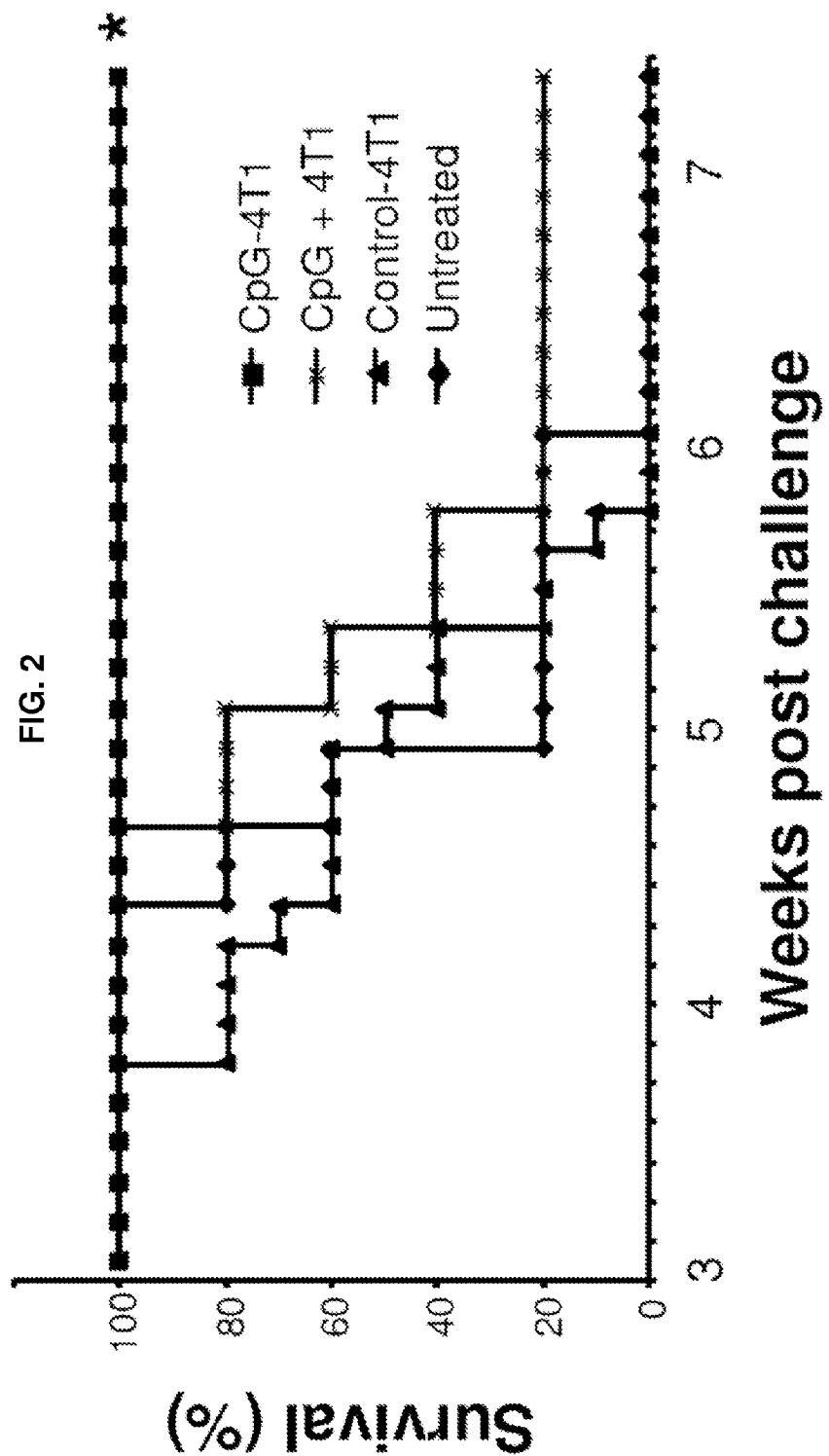
FIG. 2 is a graph illustrating the results achieved using vaccination following surgical removal of primary tumor. $5 \times 10^4$ 4T1 cells were implanted into syngeneic mice on day 0. These cells formed a tumor that was surgically removed after reaching 1 cm in diameter (typically after 2 weeks). The mice were then vaccinated i.p. with $2 \times 10^6$ 4T1 cells mixed with or conjugated to ODN. Data show survival (N=5; CpG-4T1, CpG+4T1, untreated, N=10; control-4T1 group). The experiment was repeated two times with similar results. *, $p<0.05$ (compared with all of other groups by the generalized Wilcoxon's test).

4T1 mammary carcinoma cells were implanted in the flank of syngeneic mice. 4T1 cells form large primary tumors that spontaneously metastasize to the lung, liver, lymph nodes and bone marrow (Pulanski et al., supra). After growing to >1 cm in diameter, the primary tumor (and 5 mm of surrounding tissue) was surgically removed and the mice then vaccinated. Surgical resection eliminated the primary tumor and delayed the death in control animals, but metastases arose that were uniformly lethal (FIG. 2). In contrast, mice vaccinated post-surgery with CpG-conjugated 4T1 cells were completely protected against metastatic disease (FIG. 2). Vaccination with tumor cells alone or cells mixed with free CpG ODN did not significantly reduce metastasis or prolong life (FIG. 2).

Example 4

CpG Conjugation Improves the Immunogenicity of Apoptotic Tumor Cells

The above results establish the utility of CpG-conjugated tumor cell vaccines as stand-alone therapy for established tumors and in preventing their metastatic spread following surgery. To clarify the immunologic mechanism(s) behind these effects, studies were conducted in the E.G7 tumor model. E.G7 tumor cells express OVA as a tumor-associated antigen, simplifying efforts to monitor the nature, speed and specificity of the resultant immune response (Moore et al., Cell 1988; 54:777-785).

The ability of CpG-conjugated apoptotic E.G7 cells (CpG-E.G7) to up-regulate the expression of co-stimulatory molecules by bone-marrow derived dendritic cells (BMDCs) was investigated. As seen in FIG. 3 (panels A and B), CpG-E.G7 induced a significant increase in the fraction of BMDCs expressing high levels of CD40 and CD86 (p.<0.01). This effect was not observed when BMDCs were cultured with apoptotic E.G7 cells alone or cells conjugated to control ODN (control-E.G7). CpG E.G7 also induced $CD11c^+$ DCs to produce IL-12, an effect not observed when BMDCs were cultured with control-E.G7 (p.<0.01, FIG. 3 panels C,D). The amount of IL-12 induced by CpG conjugated tumor cells was similar to that observed when BMCD were incubated with CpG ODN alone (FIG. 3, panels B and D), although studies using FITC-labeled ODN established that no free CpG was present in the conjugated tumor cell vaccine. The activation of BMDCs by CpG-E.G7 was TLR9 dependent, since BMDCs from TLR9 KO mice failed to up-regulate co-stimulatory molecule expression or produce IL-12 (FIG. 8).

Example 5

CpG Conjugated Apoptotic Tumor Cells Induce Tumor-Specific Immunity and Protect Against Tumor Development To examine the specificity of the vaccine-induced response, mice were immunized with either CpG-E.G7 or CpG-conjugated apoptotic TC-1 cells (CpG-TC-1) (these utilize OVA or papillomavirus E7 as their TAAs, respectively) and then challenged 21 days after immunization. As seen in FIG. 4 A, D, the growth of E.G7 tumors was significantly reduced by vaccination with CpG-E.G7 while the growth of TC-1 tumors was significantly reduced by vaccination with CpG-TC-1. The protection conferred by each vaccine was tumor specific, as vaccination with CpG-E.G7 had no impact on TC-1 tumor growth, and vice-versa (FIG. 4 B,E). Protection was abrogated by depletion of $CD8^+$ but not $CD4^+$ T cells, indicating that tumor specific $CD8^+$ T cells generated by CpG-conjugated vaccines were the primary mediators of tumor immunity (FIG. 4C). Tumor growth was reduced in animals vaccinated with CpG ODN mixed with (but not conjugated to) apoptotic tumor cells, but the magnitude of this effect was significantly below that induced by the CpG-conjugated vaccines and complete tumor regression never observed ($p<0.05$).

Example 6

CpG Conjugated Apoptotic Tumor Cells Induce Tumor Antigen Specific T Cells

To further elucidate the nature of the immune response induced by CpG-conjugated apoptotic tumor cells, C57Bl/6 mice were vaccinated with CpG-E.G7 and their splenocytes re-stimulated ex vivo with OVA. Vaccination with CpG-E.G7 induced a strong Th1 cytokine response, as manifest by the OVA-dependent production of IFNg (FIG. 5A). In contrast, E.G7 cells alone or control-E.G7 cells failed to induce antigen-specific immunity (FIG. 5A). Cells from mice vaccinated with a mixture of free CpG ODN plus E.G7 cells (E.G7+CpG) mounted a detectable OVA-specific response that was significantly lower than that elicited by CpG-E.G7 ($p<0.01$, FIG. 5A).

Figure 5B:
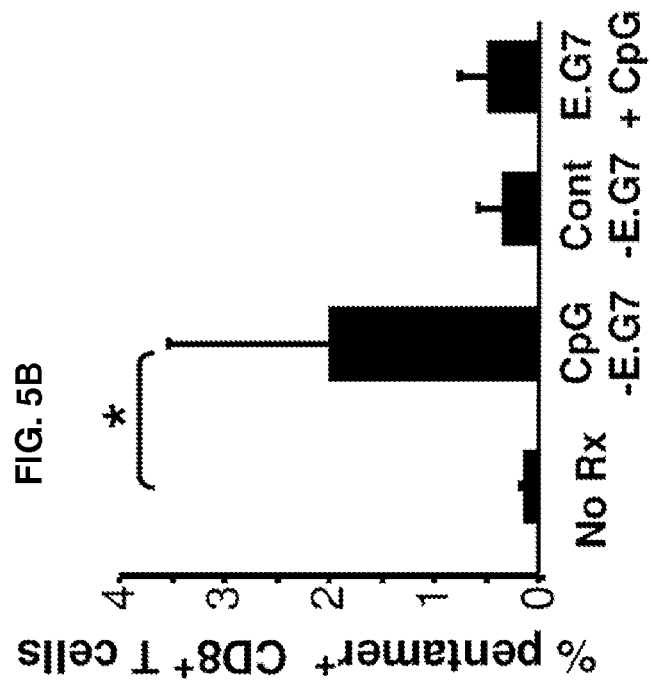
FIGS. 5A-5B are graphs showing the induction of tumor specific T cell responses by ODN-conjugated vaccine. C57Bl/6 mice were immunized i.p. on days 0 and 21 with $2 \times 10^6$ apoptotic E.G7 cells mixed with or conjugated to CpG or control ODN. A) Spleen cells were isolated on day 42, re-stimulated ex vivo with 100 ug/ml OVA and monitored for IFNg secretion. Results represent the mean+SD of 5-8 mice/group from 2 independent experiments. B) Spleen cells isolated on day 42 were stained with the SIINFEKL (SEQ ID NO: 36)/Kb pentamer and analyzed by FACS to identify OVA-specific CD8 T cells. Results represent the mean±SD of 5-7 mice/group from 3 independent experiments *, $p<0.05$, , $p<0.01$
Figure 5A:
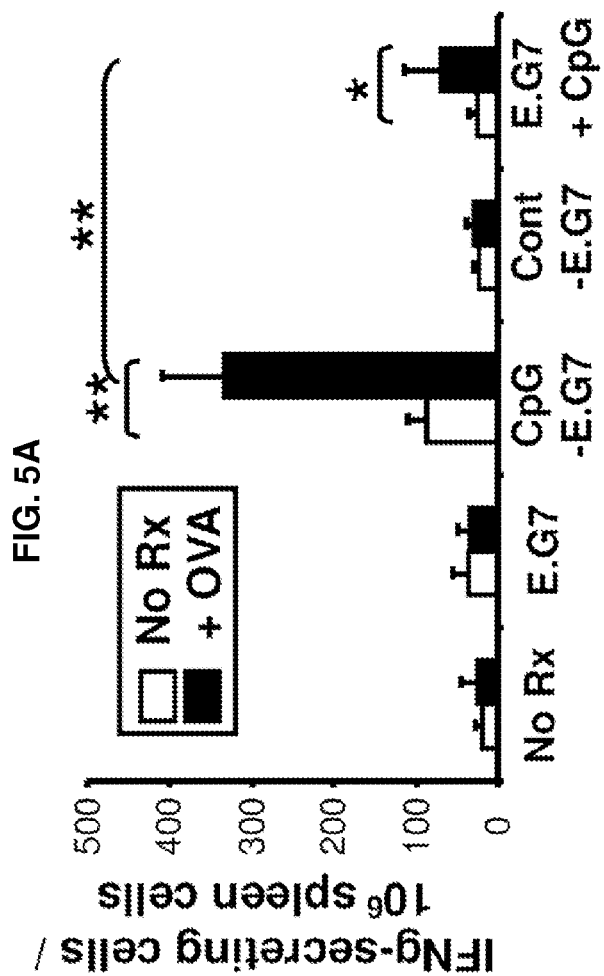
Figure 9:
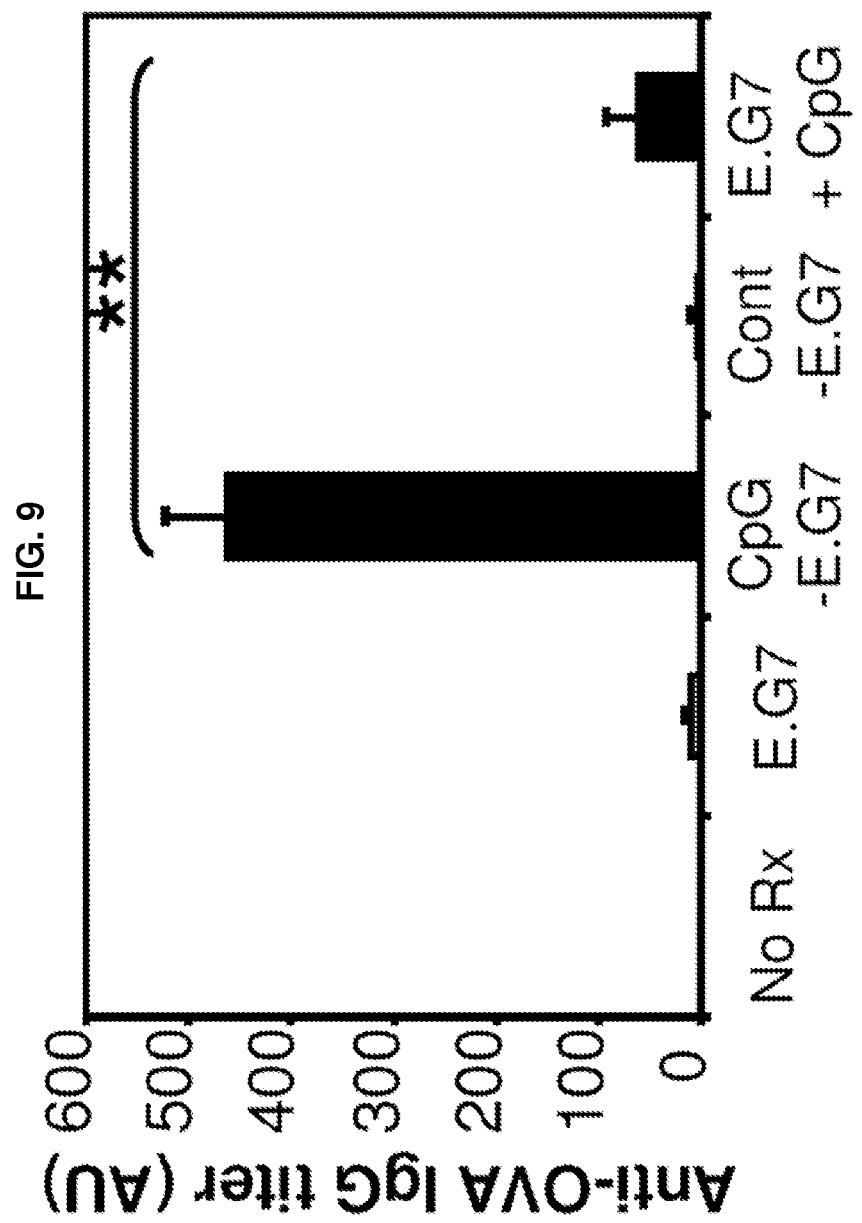
FIG. 9 is a graph showing the effect of CpG conjugated tumor cells the production of tumor antigen (Ag) specific antibody (Ab). Mice were immunized as described in FIG. 5. Six weeks later, serum from these animals was collected and analyzed by ELISA for IgG anti-OVA Ab titers. Data represent the mean±SEM of 7-8 independently analyzed mice per group. **; $p<0.01$.

Consistent with these findings, the frequency of OVA-specific T cells identified by staining spleen cells with OVA/H 2 Kb pentamers was significantly greater in mice vaccinated with CpG-E.G7 vs all relevant controls (FIG. 5B). Indeed, >2% of the CD8 T cells in mice immunized with CpG-E.G7 were pentamer-positive. This vaccination strategy also supported a significant increase in the production of OVA-specific Ab (FIG. 9) and similar results were obtained in studies involving CpG conjugated apoptotic TC-1 cells stimulated with a CD8 specific E7 peptide.

Example 7

CpG Conjugation Improves the Uptake of Apoptotic Tumor Cells by DCs and Triggers DCs Maturation CpG conjugated tumor cell vaccines were significantly more immunogenic than tumor cell vaccines mixed with free ODN. To examine the mechanism underlying this improved activity, apoptotic CSFE-labeled E.G7 cells were injected intravenously (i.v.) and the spleens of recipient mice removed and studied by FACS. As seen in FIG. 6A, E.G7 cells conjugated to either CpG or control ODN were efficiently phagocytosed by $CD11c^+$ splenocytes. The uptake of ODN-conjugated cells was 2-3 fold higher than that of unconjugated E.G7 cells ($p<0.05$, FIG. 6B). Similarly, free CpG ODN did not improve the uptake of E.G7 cells (E.G7+CpG).

The expression of CD69, an early marker of DCs activation, was significantly up-regulated by $CD11c^+$ splenocytes that internalized CpG-E.G7 ($p.<0.01$, FIG. 6C). No such effect was observed among $CD11c^+$ cells that internalized unlabeled E.G7 or E.G7 cells conjugated to control ODN, nor was CD69 up-regulated in DCs that failed to internalize CpG-E.G7 or that were treated with E.G7 plus free CpG ODN (FIG. 6D).

Figure 7:
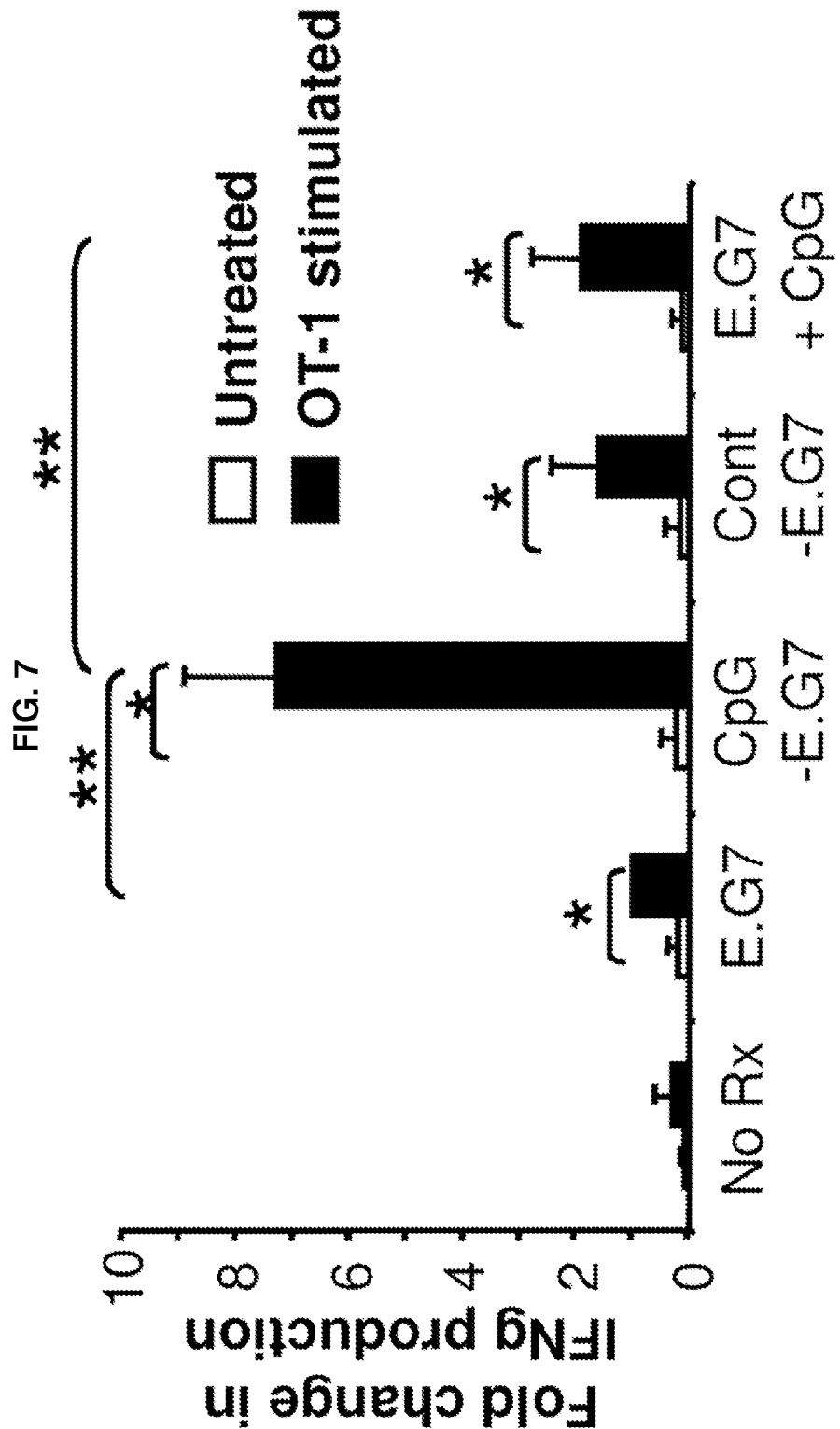
FIG. 7 is a graph showing antigen presentation by DCs isolated from vaccinated mice. C57Bl/6 mice were immunized i.p. with $10^7$ apoptotic E.G7 cells mixed with or conjugated to CpG or control ODN. Spleen cells were isolated 4 h later, and $2 \times 10^5$ DCs enriched splenocytes were co-cultured with $2 \times 10^4$ OVA-expressing OT-1 cells for 24 hours. Four independent experiments were performed, and the fold change in IFNg production in each treatment group was calculated relative to the E.G7 DCs+OT-1 group in each experiment. Results represent the mean±SD of all four experiments. *, $p<0.05$; **, $p<0.01$.

The antigen presenting ability of these DCs was then examined. $CD11c^+$ spleen cells from vaccinated mice were co-cultured with $CD8^+$ T cells from OVA-specific congenic OT-1 mice (OVA being the TAAs expressed by E.G7 cells). As expected, DCs from naive mice and mice vaccinated with E.G7 alone barely induced OT-1 cells to produce IFNg (FIG. 7). By comparison, APCs from mice vaccinated with CpG-E.G7 triggered a 7-fold increase in the number of OT-1 cells secreting IFNg ($p<0.001$). APCs from mice vaccinated with control-E.G7 induced a small increase in OT-1 activation but the magnitude of this activity was significantly below that observed in mice vaccinated with CpG-E.G7 ($p<0.01$, FIG. 7).

The results presented herein document the unexpectedly superior immunogenicity and protective activity of apoptotic tumor cell vaccines enhanced by conjugating immunostimulatory CpG ODN to their surface. Additional studies showed that prophylactic immunization with CpG-conjugated vaccines provided excellent protection in multiple tumor challenge models (including CT26, 4T1, B16 melanoma, LLC and Renca tumors).

Importantly, the progression of established TRAMP C-1 tumors was significantly slowed while the metastatic spread of 4T1 tumors (following surgical excission of the primary tumor) completely prevented when vaccination was initiated after the tumors had reached clinically detectable size. Mechanistic studies established that this strategy improved the uptake of tumor cell vaccines by APCs, triggered the functional maturation of the APCs, and promoted the generation of tumor-specific CTL.

Apoptotic tumor cells express a diverse array of TAAs. Although it has been hypnotized that the use of apoptotic tumor cells would maximize the host's ability to recognize and present tumor antigens in the context of self MHC (Stevanovic, Nat Rev Cancer 2002; 2:514-520), whole tumor cell vaccines were found to be poorly immunogenic and could even mediate immunosuppression (Green et al., Nat Rev Immunol 2009; 9:353-363; Lake, Nat Rev Cancer 2005; 5:397-405).

CpG ODN directly trigger immune cells that express TLR9, initiating an innate immune response that promotes the adaptive immunity. The adjuvant activity of CpG ODN has at least three components (see, Sano et al., J Immunol 2003; 170:2367-2373; Shirota et al., J Immunol 2001; 167: 66-74; Shirota et al., J Immunol 2002; 169:787-794): 1) a CpG-induced enhancement in APCs function, ii) CpG-dependent induction of a cytokine/chemokine microenvironment supportive of anti-tumor immunity and iii) improved antigen uptake mediated by DNA-binding receptors on APCs when the ODN is physically linked to a target antigen.

Mice vaccinated with CpG-conjugated vaccine were significantly better protected from tumor challenge than mice immunized vaccine plus free (unconjugated) CpG ODN or vaccine conjugated to control ODN (FIGS. 1, 2 and 4). The studies described herein clearly demonstrated the mechanisms underlying the enhanced immunogenicity of CpG-conjugated tumor cells. CpG conjugation improved the internalization of whole tumor based vaccines by DCs (FIG. 6). This effect was sequence independent (control ODN had the same effect), indicating that cells expressing membrane-bound ODN were more readily recognized and internalized by professional APCs. However once internalized, the presence of CpG motifs promoted the maturation and activation of these APCs, thereby significantly improving the host's anti-tumor response (FIGS. 5-7). The results demonstrate that essentially all of the DCs, which incorporated the CpG cell conjugate, were activated by CpG and strongly suggest that these cells would present antigenic TAAs for the preferential generation of tumor specific CTLs.

Previous studies designed to limit tumor growth by harnessing the adjuvant properties of CpG ODN failed to conjugate ODN to the target immunogen (Bae et al., Cancer Sci 2007; 98:747-752; Novakovic et al., Vaccine 2007; 25:8241-8256; Wu et al., J Immunother 2007; 30:789-797). Rather than conjugating CpG ODN to cell-based vaccines, free ODN were co-administered with other immune modifiers (such as GM-CSF or IL-12) (Sandler et al., Cancer Res 2003; 63:394-399; Switaj et al., Clin Cancer Res 2004; 10:4165-4175. Tumor specific immunity was only modestly improved by those efforts (see, for example Nierkens et al., Cancer Res 2008; 68:5390-5396). Heckelsmiller et al (J Immunol 2002; 169:3892-3899) co-administered free CpG ODN with apoptotic tumor cells and demonstrated that tumor-specific DCs and T cells were activated.

Only the present results document that CpG conjugation to the tumor cell vaccine dramatically increases the magnitude of this effect. FIG. 6 confirms that observation by showing that the up-regulation of CD69 expression was limited to those DCs that internalized CpG conjugated vaccine. Cross-linking ODN to antigen is a highly efficient method of insuring that vaccine and ODN consistently co-localize. In this context, the current study shows that CpG-conjugated vaccines are significantly more immunogenic than the same vaccine mixed with free ODN (FIGS. 2-3).

Tumor-specific CTL have a limited half-life and replicative capacity in vivo. Thus, eliminating established cancers and preventing the growth of metastasis may require the continuous induction of TAAs-specific CTL. Vaccines that utilize highly immunogenic vectors to elicit tumor-specific CTL cannot be administered repeatedly, as responses against the vectors interfere with subsequent recognition of the TAAs. In contrast, CpG-conjugated tumor cells continue to stimulate new CTL and boost tumor-specific immunity when administered repeatedly (FIG. 4).

A useful model to evaluate immunotherapy is provided by 4T1 mammary tumors. Similar to human breast cancer, 4T1 tumors generate frequent metastases that cause lethal disease after surgical removal of the primary tumor (Pulanski et al., Cancer Res 2000; 60:2710-2715). As seen in FIG. 2, surgery alone cannot prevent the metastatic spread of 4T1 cancer. However immunization with the CpG-conjugated 4T1 vaccine post surgery protected against metastatic disease. Effective vaccines would be prepared from fragments of the surgically resected tumors, treated to undergo apoptosis and then conjugated to CpG ODN. The results presented herein document that CpG conjugated vaccines induce a surprisingly effective protective immunity against multiple tumor cell targets, slow the growth of established tumors, and prevent the establishment of tumor metastases (FIG. 2,4).

Example 8

Use of Autologous Tumor Cells

A tumor mass is excised from a patient with cancer, such as a subject with breast cancer or prostate cancer. A suspension of the cells is generated in a media.

The apoptosis of tumor cells is induced by adding 50 ug/ml of mitomycin C (Sigma-aldrich, St. Louis, Mo.) for 24 hours at 37° in a 5% $CO_2$ in air incubator. Alternatively, tumor cells can treated with 15,000 rads can be substituted with similar effect. The treatment leads to the apoptosis of >90% of cells (as confirmed by annexin V and propidium iodide staining) within 24 hours. Mitomycin C or irradiated tumor cells never produced tumors when transferred into mice.

After the induction of apoptosis, cells are washed and incubated with 0.5-1 mg/ml of amino-modified CpG in phosphate buffered saline (PBS) for 1 hour at 4° C., followed by 5 uM of BS3, a cell-impermeable cross-linking agent for 1 hour. Under these conditions, 70-80% of the ODN bound to the surface of apoptotic cancer cell lines (established by monitoring the loss of free ODN from cell supernatants), yielding a vaccine in which 5-20 ug of ODN was conjugated to the surface of $10^6$ cells. Unbound ODN is removed completely by centrifugation. Any ODN provided above can be used. In several examples, the ODN is ODN CpG 7909, 1826 or K1555 or K3, a mixture of one, two, three or all four of these ODNs. The ODN can also be DV35, DV28, DV29 or DV113, or any combination thereof.

The conjugate is introduced back into the subject to induce tumor immunity. Tumor volume is reduced, as is the number of metastases when compared with a subject who is not administered the therapy. Symptoms are also decreased, as well as expression of tumor markers. For example, if prostate cancer is being treated, the prostate specific antigen (PSA) level is reduced.

The conjugate can be administered with other chemotherapeutic agents, which are administered either simultaneously with, or sequentially with, the conjugate.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of inducing an immune response to a tumor in a subject, comprising, selecting a subject with a tumor; and administering a therapeutically effective amount of apoptotic tumor cells conjugated to a CpG oligodexoynucleotide to the subject, wherein the CpG oligodeoxynucleotide is a K-type CpG oligodeoxynucleotide or a D-type CpG oligodeoxynucleotide wherein the K-type CpG oligodeoxynucleotide has a nucleic acid sequence set forth as:

$$5'\ N_1N_2N_3D\text{-}CpG\text{-}WN_4N_5N_6\ 3' \quad \text{(SEQ ID NO: 2)}$$

wherein the central CpG motif is unmethylated, D is T, G or A, W is A or T, and $N_1$, $N_2$, $N_3$, $N_4$, $N_5$, and $N_6$ are any nucleotide, wherein the CpG oligodeoxynucleotide is 10 to 30 nucleotides in length; and wherein the D-type CpG oligodeoxynucleotide has a sequence $$5'\text{-}X_1X_2X_3\ Pu_1\ Py_2\ CpG\ Pu_3\ Py_4\ X_4X_5X_6(W)_M\ (G)_N\text{-}3' \quad \text{(SEQ ID NO: 1)}$$

wherein the central CpG motif is unmethylated, Pu is a purine nucleotide, Py is a pyrimidine nucleotide, X and W are any nucleotide, M is any integer from 0 to 10, and N is any integer from 4 to 10, wherein the CpG ODN is 18 to 50 nucleotides in length;

thereby inducing the immune response to the tumor in the subject.

2. The method of claim 1, wherein the CpG oligodexoynucleotide is the D-type CpG oligodeoxynucleotide.

3. The method of claim 1, wherein the CpG oligodexoynucleotide is the K-type CpG oligodeoxynucleotide.

4. The method of claim 3, wherein $N_3D$ is selected from the group consisting of GpT, GpG, GpA, ApT and ApA; and $WN_4$ is selected from the group consisting of TpT or CpT.

5. The method of claim 3, wherein the K-type CpG ODN comprises SEQ ID NO: 32, SEQ ID NO: 30 or SEQ ID NO: 11.

6. The method of claim 3, wherein the K-type CpG ODN comprises one of the nucleotide sequences set forth as SEQ ID NO: 3-33 or 37.

7. The method of claim 2, wherein $Pu_1\ Py_2$ and $Pu_3\ Py_4$ are self-complementary.

8. The method of claim 2, wherein the D-type oligodeoxynucleotide comprises at least one phosphate backbone modification.

9. The method of claim 2, wherein the D-type oligodeoxynucleotide comprises at least one phosphorothioate base.

10. The method of claim 2, wherein the D-type CpG oligodeoxynucleotide comprises at least one phosphodiester base.

11. The method of claim 1, wherein the tumor is a lymphoma, cervical cancer, prostate cancer, breast cancer, colon cancer or a lung cancer.

12. The method of claim 1, wherein the immune response comprises the production of antibodies.

13. The method of claim 1, wherein the apotptoic tumor cells and the tumor are from the same type of cancer.

14. The method of claim 1, wherein the apoptotic tumor cells are autologous.

15. A method of treating a tumor in a subject, comprising, selecting a subject with a tumor; and administering a therapeutically effective amount of apoptotic tumor cells conjugated to a CpG oligodexoynucleotide to the subject, wherein the CpG oligodeoxynucleotide is a K-type CpG oligodeoxynucleotide or a D-type CpG oligodeoxynucleotide wherein the K-type CpG oligodeoxynucleotide has a nucleic acid sequence set forth as:

$$5'\ N_1N_2N_3D\text{-}CpG\text{-}WN_4N_5N_6\ 3' \quad \text{(SEQ ID NO: 2)}$$

wherein the central CpG motif is unmethylated, D is T, G or A, W is A or T, and $N_1$, $N_2$, $N_3$, $N_4$, $N_5$, and $N_6$ are any nucleotide, wherein the CpG oligodeoxynucleotide is 10 to 30 nucleotides in length; and wherein the D-type CpG oligodeoxynucleotide has a sequence $$5'\text{-}X_1X_2X_3\ Pu_1\ Py_2\ CpG\ Pu_3\ Py_4\ X_4X_5X_6(W)_M\ (G)_N\text{-}3' \quad \text{(SEQ ID NO: 1)}$$

wherein the central CpG motif is unmethylated, Pu is a purine nucleotide, Py is a pyrimidine nucleotide, X and W are any nucleotide, M is any integer from 0 to 10, and N is any integer from 4 to 10, wherein the CpG ODN is 18 to 50 nucleotides in length;

thereby treating the tumor in the subject.

16. The method of claim 15, wherein the CpG oligodexoynucleotide is the D-type CpG oligodeoxynucleotide.

17. The method of claim 15, wherein the CpG oligodexoynucleotide is the K-type CpG oligodeoxynucleotide.

18. The method of claim 17, wherein $N_3D$ is selected from the group consisting of GpT, GpG, GpA, ApT and ApA; and $WN_4$ is selected from the group consisting of TpT or CpT.

19. The method of claim 17, wherein the K-type CpG ODN comprises SEQ ID NO: 32, SEQ ID NO: 30 or SEQ ID NO: 11.

20. The method of claim 17, wherein the K-type CpG ODN comprises one of the nucleotide sequences set forth as SEQ ID NO: 3-33 or 37.

21. The method of claim 20, wherein $Pu_1\ Py_2$ and $Pu_3\ Py_4$ are self-complementary.

22. The method of claim 16, wherein the D-type oligodeoxynucleotide comprises at least one phosphate backbone modification.

23. The method of claim 16, wherein the D-type oligodeoxynucleotide comprises at least one phosphorothioate base.

24. The method of claim 16, wherein the D-type CpG oligodeoxynucleotide comprises at least one phosphodiester base.

25. The method of claim 15, wherein the tumor is a lymphoma, cervical cancer, prostate cancer, breast cancer, colon cancer or a lung cancer.

26. The method of claim 15, further comprising surgically resecting the tumor.

27. The method of claim 15, wherein the apoptotic cells are autologous.

28. A method for treating a tumor in a subject, comprising
   a. excising at least a portion of the tumor;
   b. producing a cell suspension of tumor cells from the portion of the tumor;
   c. treating the cell suspension to produce apoptotic tumor cells;

d. conjugating the apoptotic tumor cells to a CpG oligodeoxynucleotide (ODN) to form a conjugate, wherein CpG ODN is a K-type CpG oligodeoxynucleotide or a D-type ODN, wherein the K-type ODN has the nucleic acid sequence as set forth as:

(SEQ ID NO: 2)
5' $N_1N_2N_3D$-CpG-$WN_4N_5N_6$ 3' wherein the central CpG motif is unmethylated, D is T, G or A, W is A or T, and $N_1$, $N_2$, $N_3$, $N_4$, $N_5$, and $N_6$ are any nucleotides and wherein the CpG oligodeoxynucleotide is 10 to 30 nucleotides in length; and wherein the D-type CpG oligodeoxynucleotide has a sequence (SEQ ID NO: 1)
5'-$X_1X_2X_3$ $Pu_1$ $Py_2$ CpG $Pu_3$ $Py_4$ $X_4X_5X_6(W)_M$ $(G)_N$-3' wherein the central CpG motif is unmethylated, Pu is a purine nucleotide, Py is a pyrimidine nucleotide, X and W are any nucleotide, M is any integer from 0 to 10, and N is any integer from 4 to 10, wherein the CpG ODN is 18 to 50 nucleotides in length e. administering a therapeutically effective amount of the conjugate to the subject, thereby treating the subject.

29. The method of claim 28, wherein the CpG ODN is the K-type ODN, and wherein $N_3D$ is selected from the group consisting of GpT, GpG, GpA, ApT and ApA; and $WN_4$ is selected from the group consisting of TpT or CpT.

30. The method of claim 28, wherein the CpG ODN is the K-type ODN, and wherein the K-type ODN comprises the nucleic acid sequence set forth as SEQ ID NO: 32, SEQ ID NO: 30 or SEQ ID NO: 11.

31. The method of claim 28, wherein the CpG ODN is the K-type ODN, and wherein the K-type ODN comprises one of the nucleotide sequences set forth as SEQ ID NO: 3-33 or 37.

32. The method of claim 28, wherein the CpG ODN is the D-type ODN.

33. The method of claim 28, wherein the tumor is a lymphoma, cervical cancer, prostate cancer, breast cancer, colon cancer or a lung cancer.

34. The method of claim 28, wherein treating the tumor comprises decreasing tumor volume; decreasing the number of size of metastases of the tumor; or lessening a symptom of the tumor.

* * * * *

SEQUENCE LISTING

<160> NUMBER OF SEQ ID NOS: 62

<210> SEQ ID NO 1
<211> LENGTH: 32
<212> TYPE: DNA
<213> ORGANISM: Artificial Sequence
<220> FEATURE:
<223> OTHER INFORMATION: D type CpG consensus oligodeoxynucleotide
<220> FEATURE:
<221> NAME/KEY: misc_feature
<222> LOCATION: (1)..(3)
<223> OTHER INFORMATION: n is a, c, g or t
<220> FEATURE:
<221> NAME/KEY: misc_feature
<222> LOCATION: (4)..(4)
<223> OTHER INFORMATION: r is a or g
<220> FEATURE:
<221> NAME/KEY: misc_feature
<222> LOCATION: (5)..(5)
<223> OTHER INFORMATION: y is t or c
<220> FEATURE:
<221> NAME/KEY: misc_feature
<222> LOCATION: (8)..(8)
<223> OTHER INFORMATION: r is a or g
<220> FEATURE:
<221> NAME/KEY: misc_feature
<222> LOCATION: (9)..(9)
<223> OTHER INFORMATION: y is t or c
<220> FEATURE:
<221> NAME/KEY: misc_feature
<222> LOCATION: (10)..(22)
<223> OTHER INFORMATION: n is a, c, g or t
<220> FEATURE:
<221> NAME/KEY: misc_feature
<222> LOCATION: (13)..(22)
<223> OTHER INFORMATION: These nucleotides may be absent
<220> FEATURE:
<221> NAME/KEY: misc_feature
<222> LOCATION: (27)..(32)
<223> OTHER INFORMATION: These nucleotides may be absent

<400> SEQUENCE: 1
nnnrycgryn nnnnnnnnnn nnggggggggg gg                                      32

<210> SEQ ID NO 2
<211> LENGTH: 10
<212> TYPE: DNA
<213> ORGANISM: Artificial Sequence
<220> FEATURE:
<223> OTHER INFORMATION: K type CpG consensus oligodeoxynucleotide
<220> FEATURE:
<221> NAME/KEY: misc_feature
<222> LOCATION: (1)..(3)
<223> OTHER INFORMATION: n is a, c, g or t
<220> FEATURE:
<221> NAME/KEY: misc_feature
<222> LOCATION: (4)..(4)
<223> OTHER INFORMATION: d is t, g or a
<220> FEATURE:
<221> NAME/KEY: misc_feature
<222> LOCATION: (7)..(7)
<223> OTHER INFORMATION: w is a or t
<220> FEATURE:
<221> NAME/KEY: misc_feature
<222> LOCATION: (8)..(10)
<223> OTHER INFORMATION: n is a, c, g or t

<400> SEQUENCE: 2 nnndcgwnnn                                                                10

<210> SEQ ID NO 3
<211> LENGTH: 20
<212> TYPE: DNA

```
<213> ORGANISM: Artificial Sequence
<220> FEATURE:
<223> OTHER INFORMATION: Exemplary K type CpG oligodeoxynucleotide

<400> SEQUENCE: 3
ataatcgacg ttcaagcaag                                          20

<210> SEQ ID NO 4
<211> LENGTH: 13
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 4
ctcgagcgtt ctc                                                 13

<210> SEQ ID NO 5
<211> LENGTH: 14
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 5
tctcgagcgt tctc                                                14

<210> SEQ ID NO 6
<211> LENGTH: 16
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 6
actctggagc gttctc                                              16

<210> SEQ ID NO 7
<211> LENGTH: 12
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 7
tgcagcgttc tc                                                  12

<210> SEQ ID NO 8
<211> LENGTH: 12
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 8
tcgaggcttc tc                                                  12

<210> SEQ ID NO 9
<211> LENGTH: 12
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 9
gtcggcgttg ac                                                  12
```

```
<210> SEQ ID NO 10
<211> LENGTH: 19
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 10
tcgactctcg agcgttctc                                                    19

<210> SEQ ID NO 11
<211> LENGTH: 20
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 11
atcgactctc gagcgttctc                                                   20

<210> SEQ ID NO 12
<211> LENGTH: 12
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 12
tcgagcgttc tc                                                           12

<210> SEQ ID NO 13
<211> LENGTH: 12
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 13
gtcggcgtcg ac                                                           12

<210> SEQ ID NO 14
<211> LENGTH: 12
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 14
gtcgacgttg ac                                                           12

<210> SEQ ID NO 15
<211> LENGTH: 16
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 15
actctcgagg gttctc                                                       16

<210> SEQ ID NO 16
<211> LENGTH: 16
<212> TYPE: DNA
<213> ORGANISM: Artificial Sequence
<220> FEATURE:
<223> OTHER INFORMATION: Exemplary K type CpG oligodeoxynucleotide
```

-continued

```
<400> SEQUENCE: 16
actctcgagc gttctc                                                        16

<210> SEQ ID NO 17
<211> LENGTH: 12
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 17
gtcgtcgatg ac                                                            12

<210> SEQ ID NO 18
<211> LENGTH: 12
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 18
gtcgacgctg ac                                                            12

<210> SEQ ID NO 19
<211> LENGTH: 12
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 19
gtcgacgtcg ac                                                            12

<210> SEQ ID NO 20
<211> LENGTH: 12
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 20
gtcatcgatg ca                                                            12

<210> SEQ ID NO 21
<211> LENGTH: 12
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 21
gtcagcgtcg ac                                                            12

<210> SEQ ID NO 22
<211> LENGTH: 11
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 22
tcgagcgttc t                                                             11

<210> SEQ ID NO 23
<211> LENGTH: 16
<212> TYPE: DNA
```

```
<213> ORGANISM: Artificial Sequence
<220> FEATURE:
<223> OTHER INFORMATION: Exemplary K type CpG oligodeoxynucleotide

<400> SEQUENCE: 23
actctggagc gttctc                                                   16

<210> SEQ ID NO 24
<211> LENGTH: 16
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 24
actctcgagg gttctc                                                   16

<210> SEQ ID NO 25
<211> LENGTH: 16
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 25
actctcgagc gttcta                                                   16

<210> SEQ ID NO 26
<211> LENGTH: 16
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 26
catctcgagc gttctc                                                   16

<210> SEQ ID NO 27
<211> LENGTH: 14
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 27
actctttcgt tctc                                                     14

<210> SEQ ID NO 28
<211> LENGTH: 11
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 28
tcgagcgttc t                                                        11

<210> SEQ ID NO 29
<211> LENGTH: 12
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 29
tcgttcgttc tc                                                       12
```

```
<210> SEQ ID NO 30
<211> LENGTH: 15
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 30
gctagacgtt agcgt                                                    15

<210> SEQ ID NO 31
<211> LENGTH: 12
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 31
tcgaggcttc tc                                                       12

<210> SEQ ID NO 32
<211> LENGTH: 20
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 32
tccatgacgt tcctgacgtt                                               20

<210> SEQ ID NO 33
<211> LENGTH: 24
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 33
tcgtcgtttt gtcgttttgt cgtt                                          24

<210> SEQ ID NO 34
<211> LENGTH: 15
<212> TYPE: DNA
<213> ORGANISM: Artificial Sequence
<220> FEATURE:
<223> OTHER INFORMATION: Control oligodeoxynucleotide

<400> SEQUENCE: 34
tagagcttag cttgc                                                    15

<210> SEQ ID NO 35
<211> LENGTH: 20
<212> TYPE: DNA
<213> ORGANISM: Artificial Sequence
<220> FEATURE:
<223> OTHER INFORMATION: Control oligodeoxynucleotide

<400> SEQUENCE: 35
tccatgagct tcctgagtct                                               20

<210> SEQ ID NO 36
<211> LENGTH: 8
<212> TYPE: PRT
<213> ORGANISM: Artificial Sequence
<220> FEATURE:
<223> OTHER INFORMATION: Synthetic Peptide
```

<400> SEQUENCE: 36

Ser Ile Ile Asn Phe Glu Lys Leu
1               5

<210> SEQ ID NO 37
<211> LENGTH: 24
<212> TYPE: DNA
<213> ORGANISM: Artificial Sequence
<220> FEATURE:
<223> OTHER INFORMATION: Exemplary K type CpG oligodeoxynucleotide

<400> SEQUENCE: 37
tcgtcgtttt acggcgccgt gccg                                          24

<210> SEQ ID NO 38
<211> LENGTH: 20
<212> TYPE: DNA
<213> ORGANISM: Artificial Sequence
<220> FEATURE:
<223> OTHER INFORMATION: Exemplary D type CpG oligodeoxynucleotide

<400> SEQUENCE: 38
ggtgcatcga tacaggggggg                                              20

<210> SEQ ID NO 39
<211> LENGTH: 20
<212> TYPE: DNA
<213> ORGANISM: Artificial Sequence
<220> FEATURE:
<223> OTHER INFORMATION: Exemplary D type CpG oligodeoxynucleotide

<400> SEQUENCE: 39
ggtgcgtcga tgcaggggggg                                              20

<210> SEQ ID NO 40
<211> LENGTH: 20
<212> TYPE: DNA
<213> ORGANISM: Artificial Sequence
<220> FEATURE:
<223> OTHER INFORMATION: Exemplary D type CpG oligodeoxynucleotide

<400> SEQUENCE: 40
ggtgcatcga tgcaggggggg                                              20

<210> SEQ ID NO 41
<211> LENGTH: 20
<212> TYPE: DNA
<213> ORGANISM: Artificial Sequence
<220> FEATURE:
<223> OTHER INFORMATION: Exemplary D type CpG oligodeoxynucleotide

<400> SEQUENCE: 41
ggtgcaccgg tgcaggggggg                                              20

<210> SEQ ID NO 42
<211> LENGTH: 20
<212> TYPE: DNA
<213> ORGANISM: Artificial Sequence
<220> FEATURE:
<223> OTHER INFORMATION: Exemplary D type CpG oligodeoxynucleotide

<400> SEQUENCE: 42
ggtgtgtcga tgcaggggggg                                              20

<210> SEQ ID NO 43
<211> LENGTH: 18

```
<212> TYPE: DNA
<213> ORGANISM: Artificial Sequence
<220> FEATURE:
<223> OTHER INFORMATION: Exemplary D type CpG oligodeoxynucleotide

<400> SEQUENCE: 43
tgcatcgatg caggggggg                                                    18

<210> SEQ ID NO 44
<211> LENGTH: 20
<212> TYPE: DNA
<213> ORGANISM: Artificial Sequence
<220> FEATURE:
<223> OTHER INFORMATION: Exemplary D type CpG oligodeoxynucleotide

<400> SEQUENCE: 44
ggtgcatcga tgcaggggggg                                                  20

<210> SEQ ID NO 45
<211> LENGTH: 20
<212> TYPE: DNA
<213> ORGANISM: Artificial Sequence
<220> FEATURE:
<223> OTHER INFORMATION: Exemplary D type CpG oligodeoxynucleotide

<400> SEQUENCE: 45
ggtgcatcgt tgcaggggggg                                                  20

<210> SEQ ID NO 46
<211> LENGTH: 20
<212> TYPE: DNA
<213> ORGANISM: Artificial Sequence
<220> FEATURE:
<223> OTHER INFORMATION: Exemplary D type CpG oligodeoxynucleotide

<400> SEQUENCE: 46
ggtgcgtcga cgcaggggggg                                                  20

<210> SEQ ID NO 47
<211> LENGTH: 20
<212> TYPE: DNA
<213> ORGANISM: Artificial Sequence
<220> FEATURE:
<223> OTHER INFORMATION: Exemplary D type CpG oligodeoxynucleotide

<400> SEQUENCE: 47
ggtcgatcga tgcacggggg                                                   20

<210> SEQ ID NO 48
<211> LENGTH: 20
<212> TYPE: DNA
<213> ORGANISM: Artificial Sequence
<220> FEATURE:
<223> OTHER INFORMATION: Exemplary D type CpG oligodeoxynucleotide

<400> SEQUENCE: 48
ggtgcatcga tgcaggggggg                                                  20

<210> SEQ ID NO 49
<211> LENGTH: 20
<212> TYPE: DNA
<213> ORGANISM: Artificial Sequence
<220> FEATURE:
<223> OTHER INFORMATION: Exemplary D type CpG oligodeoxynucleotide

<400> SEQUENCE: 49
ggtgcatcga cgcaggggggg                                                  20
```

<210> SEQ ID NO 50
<211> LENGTH: 20
<212> TYPE: DNA
<213> ORGANISM: Artificial Sequence
<220> FEATURE:
<223> OTHER INFORMATION: Exemplary D type CpG oligodeoxynucleotide

<400> SEQUENCE: 50
ggtgcatcga taggcgggggg                                              20

<210> SEQ ID NO 51
<211> LENGTH: 20
<212> TYPE: DNA
<213> ORGANISM: Artificial Sequence
<220> FEATURE:
<223> OTHER INFORMATION: Exemplary D type CpG oligodeoxynucleotide

<400> SEQUENCE: 51
ggtgcaccga tgcagggggg                                               20

<210> SEQ ID NO 52
<211> LENGTH: 20
<212> TYPE: DNA
<213> ORGANISM: Artificial Sequence
<220> FEATURE:
<223> OTHER INFORMATION: Exemplary D type CpG oligodeoxynucleotide

<400> SEQUENCE: 52
cctgcatcga tgcagggggg                                               20

<210> SEQ ID NO 53
<211> LENGTH: 20
<212> TYPE: DNA
<213> ORGANISM: Artificial Sequence
<220> FEATURE:
<223> OTHER INFORMATION: Exemplary D type CpG oligodeoxynucleotide

<400> SEQUENCE: 53
ggtatatcga tatagggggg                                               20

<210> SEQ ID NO 54
<211> LENGTH: 20
<212> TYPE: DNA
<213> ORGANISM: Artificial Sequence
<220> FEATURE:
<223> OTHER INFORMATION: Exemplary D type CpG oligodeoxynucleotide

<400> SEQUENCE: 54
ggtggatcga tccagggggg                                               20

<210> SEQ ID NO 55
<211> LENGTH: 20
<212> TYPE: DNA
<213> ORGANISM: Artificial Sequence
<220> FEATURE:
<223> OTHER INFORMATION: Exemplary D type CpG oligodeoxynucleotide
<220> FEATURE:
<221> NAME/KEY: misc_feature
<222> LOCATION: (1)..(2)
<223> OTHER INFORMATION: n is a, c, g or t
<220> FEATURE:
<221> NAME/KEY: misc_feature
<222> LOCATION: (1)..(2)
<223> OTHER INFORMATION: These nucleotides may be absent

<400> SEQUENCE: 55
nntgcatcga tgcagggggg                                               20

```
<210> SEQ ID NO 56
<211> LENGTH: 20
<212> TYPE: DNA
<213> ORGANISM: Artificial Sequence
<220> FEATURE:
<223> OTHER INFORMATION: Exemplary D type CpG oligodeoxynucleotide
<220> FEATURE:
<221> NAME/KEY: misc_feature
<222> LOCATION: (1)..(2)
<223> OTHER INFORMATION: n is a, c, g or t
<220> FEATURE:
<221> NAME/KEY: misc_feature
<222> LOCATION: (1)..(2)
<223> OTHER INFORMATION: These nucleotides may be absent

<400> SEQUENCE: 56
nntgcaccgg tgcagggggg                                              20

<210> SEQ ID NO 57
<211> LENGTH: 20
<212> TYPE: DNA
<213> ORGANISM: Artificial Sequence
<220> FEATURE:
<223> OTHER INFORMATION: Exemplary D type CpG oligodeoxynucleotide
<220> FEATURE:
<221> NAME/KEY: misc_feature
<222> LOCATION: (1)..(2)
<223> OTHER INFORMATION: n is a, c, g or t
<220> FEATURE:
<221> NAME/KEY: misc_feature
<222> LOCATION: (1)..(2)
<223> OTHER INFORMATION: These nucleotides may be absent

<400> SEQUENCE: 57
nntgcgtcga cgcagggggg                                              20

<210> SEQ ID NO 58
<211> LENGTH: 20
<212> TYPE: DNA
<213> ORGANISM: Artificial Sequence
<220> FEATURE:
<223> OTHER INFORMATION: Exemplary D type CpG oligodeoxynucleotide
<220> FEATURE:
<221> NAME/KEY: misc_feature
<222> LOCATION: (1)..(2)
<223> OTHER INFORMATION: n is a, c, g or t
<220> FEATURE:
<221> NAME/KEY: misc_feature
<222> LOCATION: (1)..(2)
<223> OTHER INFORMATION: These nucleotides may be absent

<400> SEQUENCE: 58
nntgcgtcga tgcagggggg                                              20

<210> SEQ ID NO 59
<211> LENGTH: 20
<212> TYPE: DNA
<213> ORGANISM: Artificial Sequence
<220> FEATURE:
<223> OTHER INFORMATION: Exemplary D type CpG oligodeoxynucleotide
<220> FEATURE:
<221> NAME/KEY: misc_feature
<222> LOCATION: (1)..(2)
<223> OTHER INFORMATION: n is a, c, g or t
```

```
<220> FEATURE:
<221> NAME/KEY: misc_feature
<222> LOCATION: (1)..(2)
<223> OTHER INFORMATION: These nucleotides may be absent

<400> SEQUENCE: 59
nntgcgccgg cgcagggggg                                                    20

<210> SEQ ID NO 60
<211> LENGTH: 20
<212> TYPE: DNA
<213> ORGANISM: Artificial Sequence
<220> FEATURE:
<223> OTHER INFORMATION: Exemplary D type CpG oligodeoxynucleotide
<220> FEATURE:
<221> NAME/KEY: misc_feature
<222> LOCATION: (1)..(2)
<223> OTHER INFORMATION: n is a, c, g or t
<220> FEATURE:
<221> NAME/KEY: misc_feature
<222> LOCATION: (1)..(2)
<223> OTHER INFORMATION: These nucleotides may be absent

<400> SEQUENCE: 60
nntgcgccga tgcagggggg                                                    20

<210> SEQ ID NO 61
<211> LENGTH: 20
<212> TYPE: DNA
<213> ORGANISM: Artificial Sequence
<220> FEATURE:
<223> OTHER INFORMATION: Exemplary D type CpG oligodeoxynucleotide
<220> FEATURE:
<221> NAME/KEY: misc_feature
<222> LOCATION: (1)..(2)
<223> OTHER INFORMATION: n is a, c, g or t
<220> FEATURE:
<221> NAME/KEY: misc_feature
<222> LOCATION: (1)..(2)
<223> OTHER INFORMATION: These nucleotides may be absent

<400> SEQUENCE: 61
nntgcatcga cgcagggggg                                                    20

<210> SEQ ID NO 62
<211> LENGTH: 20
<212> TYPE: DNA
<213> ORGANISM: Artificial Sequence
<220> FEATURE:
<223> OTHER INFORMATION: Exemplary D type CpG oligodeoxynucleotide
<220> FEATURE:
<221> NAME/KEY: misc_feature
<222> LOCATION: (1)..(2)
<223> OTHER INFORMATION: n is a, c, g or t
<220> FEATURE:
<221> NAME/KEY: misc_feature
<222> LOCATION: (1)..(2)
<223> OTHER INFORMATION: These nucleotides may be absent

<400> SEQUENCE: 62
nntgcgtcgg tgcagggggg                                                    20
```